(12) United States Patent
Kelly

(10) Patent No.: US 6,277,813 B1
(45) Date of Patent: Aug. 21, 2001

(54) COLOSTRUM DERIVED GROWTH FACTOR

(75) Inventor: Denise Kelly, Aberdeen (GB)

(73) Assignee: The Rowett Research Institute, Aberdeen (GB)

( * ) Notice: Subject to any disclaimer, the term of this patent is extended or adjusted under 35 U.S.C. 154(b) by 0 days.

(21) Appl. No.: 08/983,537

(22) PCT Filed: Jul. 15, 1996

(86) PCT No.: PCT/GN96/01686

§ 371 Date: Jul. 29, 1998

§ 102(e) Date: Jul. 29, 1998

(87) PCT Pub. No.: WO97/04009

PCT Pub. Date: Feb. 6, 1997

(30) Foreign Application Priority Data

Jul. 15, 1995 (GB) .................................................. 9514580
Jul. 19, 1995 (GB) .................................................. 9514835

(51) Int. Cl.[7] .......................... C07K 14/475; A61K 38/18
(52) U.S. Cl. ................ 514/2; 530/399; 530/412
(58) Field of Search ..................................... 530/399, 350, 530/412; 514/2

(56) References Cited

PUBLICATIONS

Database WPI, Section Ch, Week 9631, Derwent Publications Ltd., Class B04, AN 96–306444, XP002017833 & JP,A,08 133 943 (Kyodo Nyugyo KK), May 28, 1996.
Burrin et al., "Nutrient–Independent and Nutrient–Dependent Factors Stimulate Protein Synthesis in Colostrum–Fed Newborn Pigs", Pediatric Research, vol. 37, No. 5, May 1995, p. 593–599.

*Primary Examiner*—Christine J. Saoud
(74) *Attorney, Agent, or Firm*—Ratner & Prestia

(57) ABSTRACT

The present invention relates to a polypeptide growth factor derived from colostrum (CDGF) having defined chemical and biological characteristics. The factor may be prepared from porcine or bovine colostrum and pharmaceutical uses thereof may include combatting invasion of the body by pathogens, wound healing, promoting organ growth and development and promoting adaption of the gastrointestinal tract to diet change.

6 Claims, 32 Drawing Sheets

Effect of Preclosure Colostrum Intake on Intestinal Lactase

Bioactive Substances in Colostrum and Milk

| | |
|---|---|
| Pituitary Hormones | Prolactin, Growth hormone, Oxytocin |
| Hypothalamic Hormones | Somatostatin, Growth Hormone Releasing Hormone |
| Growth Factors | IGF, NGF, EGF, TGFα, TGFβ, PDGF, Relaxin, Calcitonin |
| Steroid Hormones | Estradiol, Progesterone, Testosterone, Corticosterone |
| Gastrointestinal Peptides | VIP, Bombesin, Cholecystokinin, Gastrin, Substance P, Neurotensin |
| Others | Prostaglandins, Transferrin, Lactoferrin |

Fig. 5

Phosphorylation of newborn and suckled microvillar membrane proteins by IGF1 and defatted colostrum
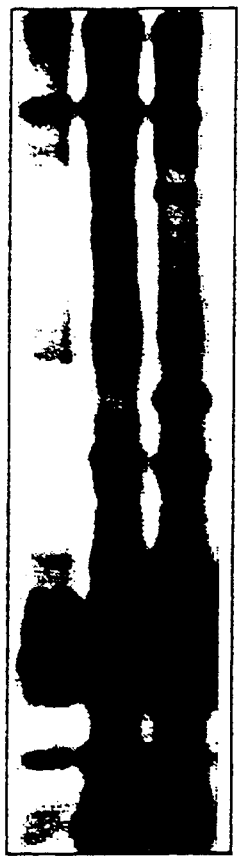
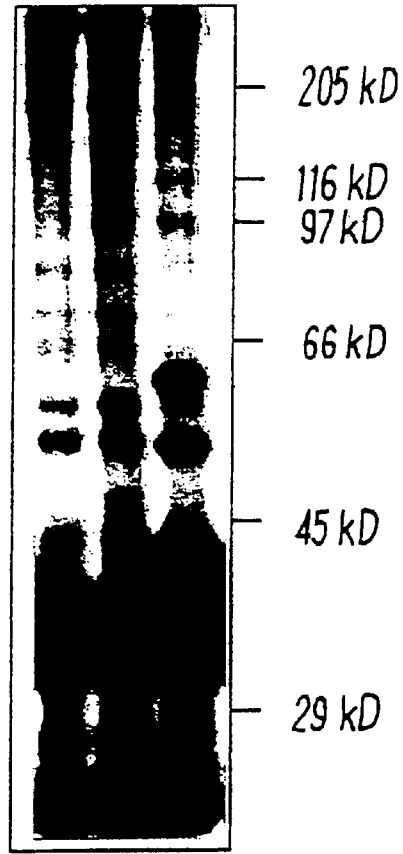
C  IGF  COL
newborn
C  IGF  COL
suckled
— 205 kD
— 116 kD
— 97 kD
— 66 kD
— 45 kD
— 29 kD
C — Control
COL — Defatted colostrum
FIG. 7

Phosphorylation of newborn, suckled and weaned microvillar membranes

WGA-Purified BBMV

N   Col   S

FIG. 9

Protein Kinase Inhibition

Tyrphostin  C Col   C Col   C Col   C Col
           B46     B48     B50     B56

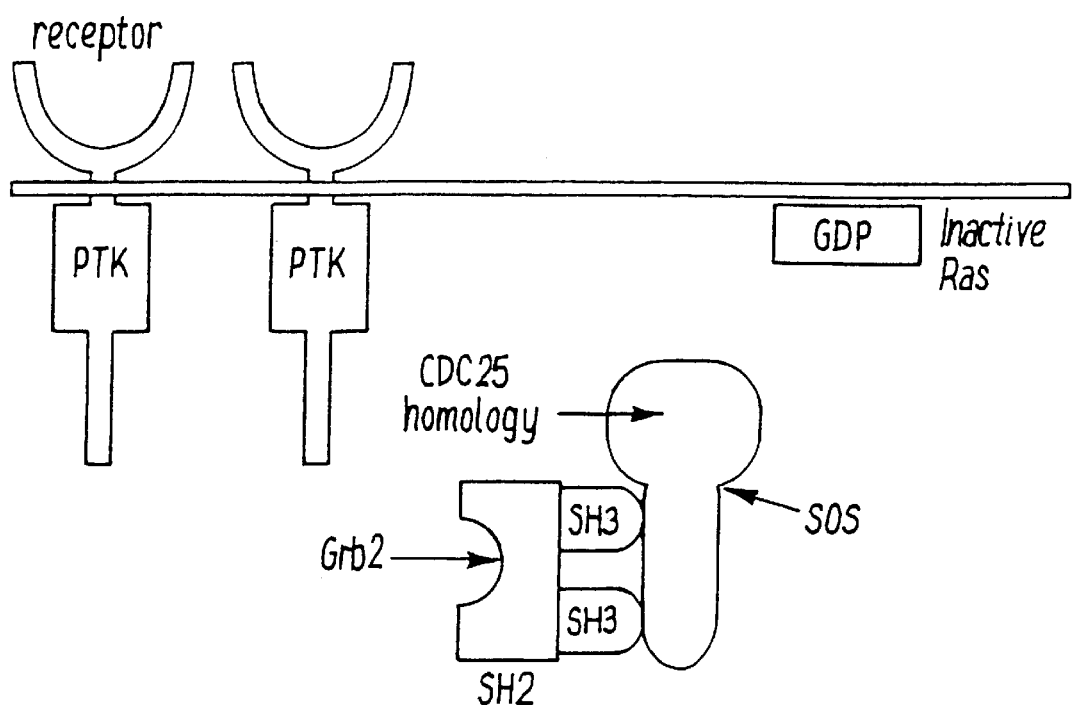
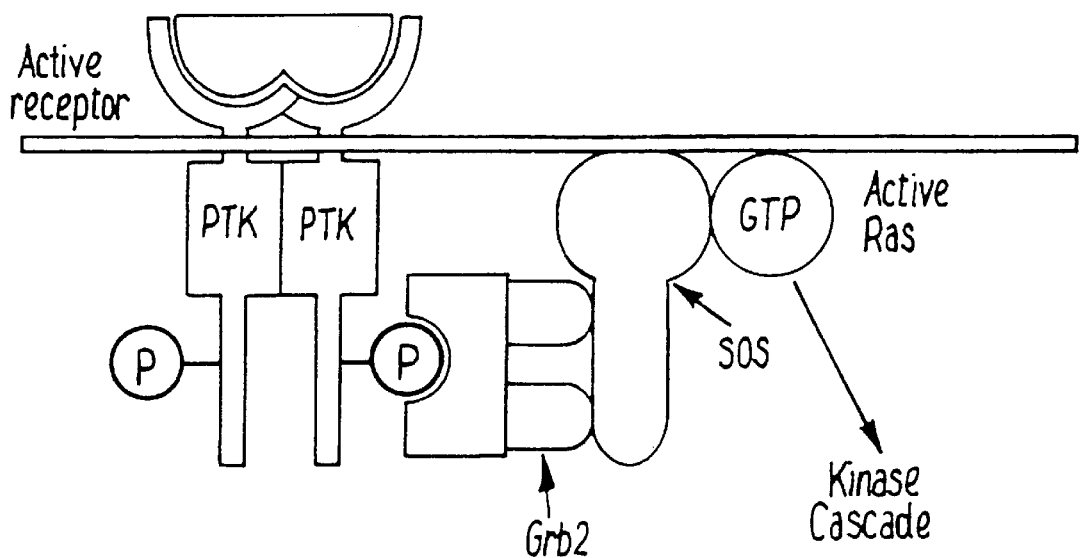
FIG. 14

Purification of GAP complex

C    Col

Annexin and Cytokeratin purification

*Growth Factor Phosphorylation of Microvillar Membrane Proteins*

Colostrum Purification
Protein - Coomassie blue stain
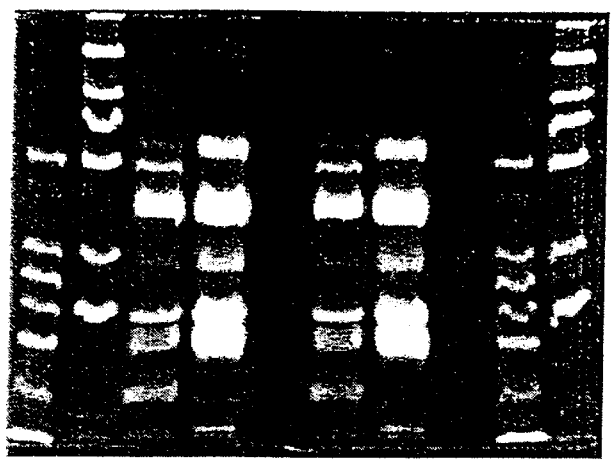
A  B  C  D  E  F  G  H  I  J
Protein - Silver Stain
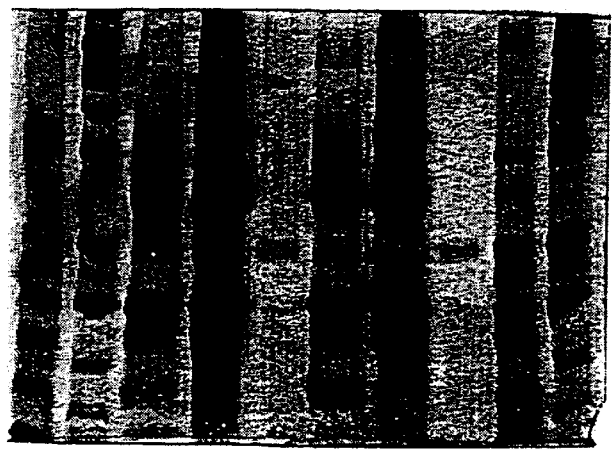
A  B  C  D  E  F  G  H  I  J
A,J - Low molecular weight standards
B,I - High molecular weight standards
C,F - Defatted acellular colostrum
D,G - Colostrum fraction (F5) from gel filtration column
E,H - Fraction F5 following DTT/heat treatment
FIG. 22b

COLOSTRUM DERIVED GROWTH FACTOR

This Application is the U.S. national stage entry of PCT/GB96/01686, filed Jul. 15, 1996.

The present invention relates to a novel growth factor present in colostrum, to a composition comprising said growth factor and the pharmaceutical uses thereof.

The present invention provides the novel polypeptide CDGF (colostrum derived growth factor).

Further, the present invention provides the use of CDGF in medical and veterinary applications. In particular, the present invention provides the use of CDGF to promote the growth and/or function of tissues as well as the use of CDGF to combat or alleviate disease states or abnormalities. Thus CDGF may have particular utility for wound healing applications (for example following accidents or surgery) and to combat or alleviate disease conditions where tissue regeneration is required (for example ulcers). CDGF may also be of utility in combating deleterious side effects of other drug regimes, in particular in decreasing the side effects of chemotherapy or radiotherapy treatment for cancer, especially in combating the influence of such treatments on the gastrointestinal tract. CDGF is believed to be of particular utility for tissue derived from the gastrointestinal tract, skeletal muscle, liver and glandular tissue (especially the mammary gland), but the invention is not limited to use in respect of these organs alone.

In more detail, CDGF may be helpful in treating post-operative patients to promote healthy tissue regeneration, and CDGF treatment following the surgical removal of tumours is believed to be particularly beneficial.

One of the effects of CDGF is to promote tight junctions between the cells lining the gastrointestinal tract. This is of importance for pre-term neonates, which will possess an immature and "leaky" intestine (ie the junctions between the cells of the intestine are not sufficiently tight). This in turn can affect the absorbance of nutrients. Likewise neonates which are atopic (and are thus prone to allergy) have also been shown to have immature "leaky" intestines. Administration of CDGF (either as a medicament or as a food supplement) may therefore be advantageous in promoting the maturation of the gastrointestinal tract of such neonates.

In a related manner, patients requiring total parenteral nutrition (tpn) may benefit from receiving CDGF, either in a separate formulation or as a component of the tpn composition.

With regard to the gastrointestinal tract, CDGF may:
a) Promote the regeneration of damaged tissue.
b) Promote intestinal and body function of pre-term neonates, nutritionally compromised neonates
c) Promote the barrier function of the gastrointestinal tact, thus enhancing disease resistance.
d) Combat intestinal colonisation by micro-organism (especially bacterial) pathogens.

In another aspect the present invention provides a composition comprising CDGF together with an inert carrier or excipient.

Desirably the composition may be formulated for therapeutic applications (including prophylactic therapeutic applications), and the carrier or excipient should-be chosen accordingly.

Alternatively the composition may be formulated as a food supplement or food substance. For example, the present invention includes baby food formulations comprising CDGF and also tpn formulations or invalid food formulations comprising CDGF.

In addition to CDGF the composition may comprise other ingredients. Mention may be made of inter alia, biologically active ingredients (for example antibiotics; other growth factors such as IGF, EGF, FGF or PDGF including combinations of cytokines with amino acids or polyamines (for example IGF/glutamine combinations); insulin; cytokines for example interleukins or any other agent having a biologically desirable effect), viscosity adjusting agents; osmosity adjusting agents, buffers, pH adjusting agents, flavourings, stabilisers, colourings, preservations and the like. Delayed release or controlled release formulations are also included.

The composition of the present invention may be formulated for administration by any suitable means. Particular mention may be made of oral, enteral, parenteral, subcutaneous and nasal routes of administrations. The composition may be prepared as a spray, solution, suspension, colloid, concentrate, powder, granules, tablets, pressed tablets, capsules (including coated and uncoated tablets and capsules), suppository and the like. Delayed release or controlled release formulations are also included.

Advantageously the composition will be sterile, and will be suitable for medical use.

The composition may be used as outlined above for CDGF, and such use forms a further aspect of the present invention.

In another aspect the present invention provides the use of CDGF or in the manufacture of a medicament for pharmaceutical use.

In a yet further aspect the present invention provides a method of treatment of the human or non-human (preferably mammalian) animal body, said method comprising administering a therapeutically effective amount of CDGF or a composition comprising CDGF to said body.

The method of treatment described above may be to combat invasion of the body (especially the gastrointestinal tract) by pathogens; to promote wound healing; to promote organ (for example intestinal) growth and development (especially in neonates or nutritionally or disease compromised adults). The method may also be of utility in promoting adaptation of the gastrointestinal tract to a change in diet.

Reference is made above to the polypeptide CDGF. This polypeptide (the term "polypeptide" as used herein refers to any peptide molecule, regardless of molecular size, shape or construction) is an active factor derived from colostrum. Porcine colostrum is mentioned as a suitable source of CDGF. CDGF is initially found to be bound to a large carrier molecule, giving an apparent molecular weight of over 200 kDa.

CDGF has been measured to have a molecular weight in the range of 60–80 kDa. CDGF is hydrophobic.

CDGF has been found to have the following physical characteristics:
1) Activity abolished by proteolytic enzymes (trypsin).
2) Essentially heat stable (over 70% activity retained) after heating to 100° C. for 10 minutes.
3) Stable in 2.4M formic acid.
4) Stable and soluble in 100% of 0.1% trifluoroacetic acid.
5) Activity is retained after treatment with 50 mM dithiothreitol.
6) Stable in 50% acetonitrile.
7) Stable and soluble in 50% ethanol.

The purification of CDGF from porcine colostrum is described in detail in the Examples. However, the process may be briefly summarised as follows:
a) separation of all components of colostrum having a molecular weight of over 200 kDa. (Components having a molecular weight below this cut-off are discarded);

b) treatment of the product of step (a) with dithiothreitol and boiled for 10 minutes; and c) The mixture of step (b) is centrifuged to spin down any precipitated matter; CDGF is located in the supernatant.

CDGF may be identified as providing the following biological effects:

1) Stimulates proliferation of intestinal cells in in vitro cultures.
2) Promotes the differentiation of intestinal cells as measured by lactase activity and protein glycosylation.
3) Phosphorylation of membrane proteins of MVM vesicles in the phosphorylation assay described in the Examples.
4) Stimulation of the Ras pathway via GAP in MVM vesicles.
5) Stimulation of the genes c-myc and fos.

The present invention will now be further described with reference to the following, non-limiting, Examples and drawings in which.

FIG. 5 lists bioactive hormones and growth factors present in colostrum.

Figure 6:
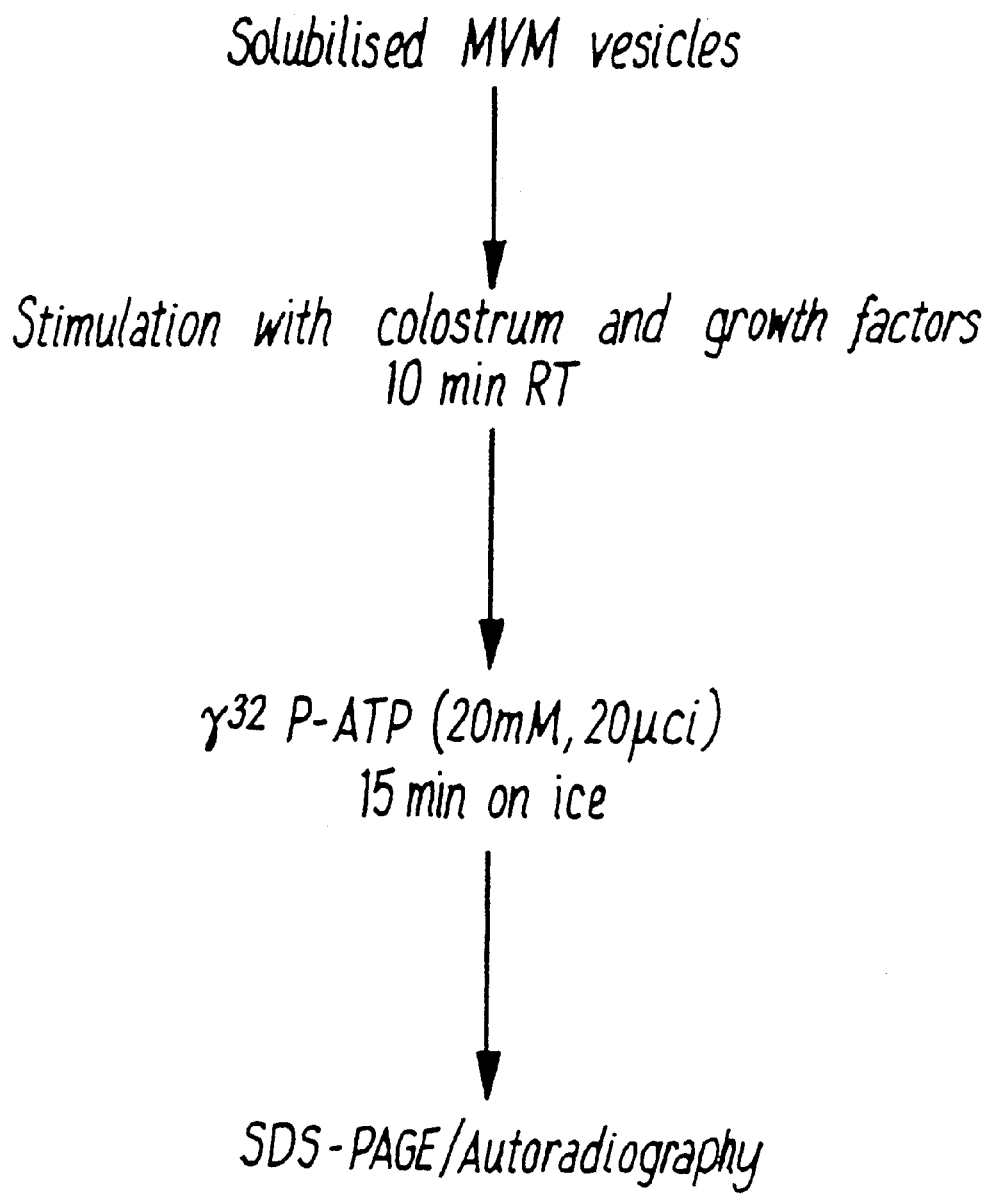

FIG. 6 is a schematic representation of the phosphorylation bioassay described in Example 2.

FIG. 7 shows the phosphorylation of microvillar membrane proteins by IGF1 and defatted colostrum.

Figure 8:
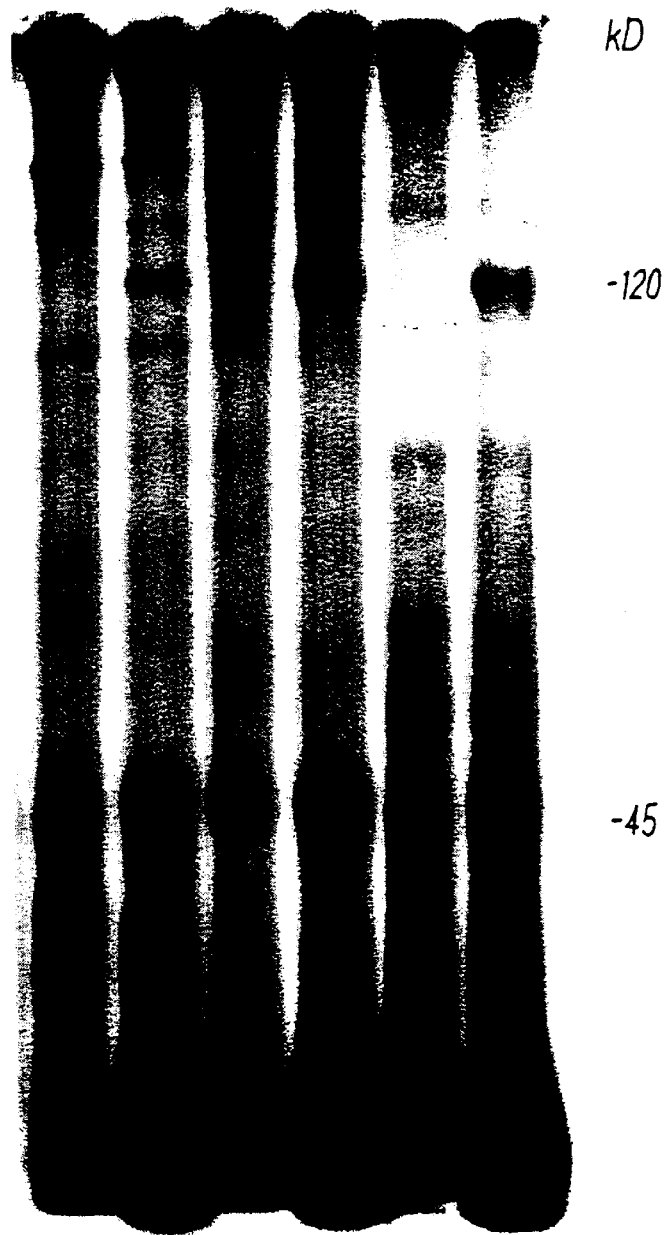

FIG. 8 shows the phosphorylation of microvillar membrane proteins in newborn, suckled and weaned animals.

Figure 9:
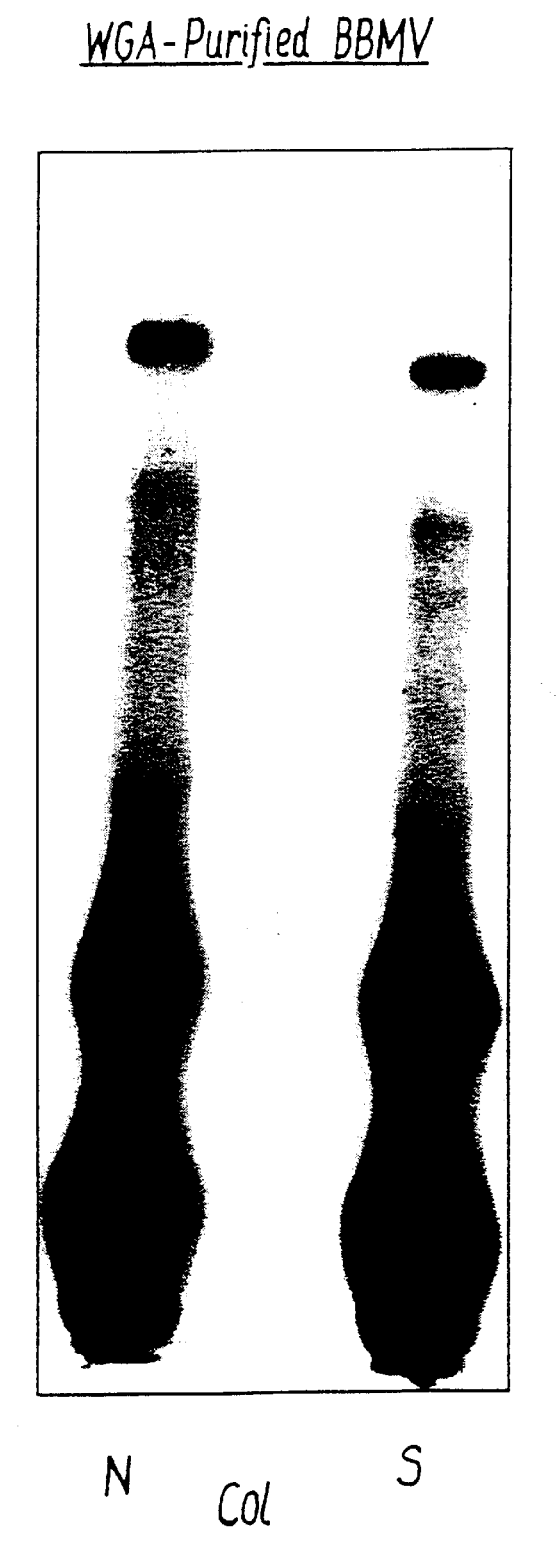

FIG. 9 shows the phosphorylation of WGA-purified micro-villar membrane proteins in newborn and suckled animal.

Figure 10:
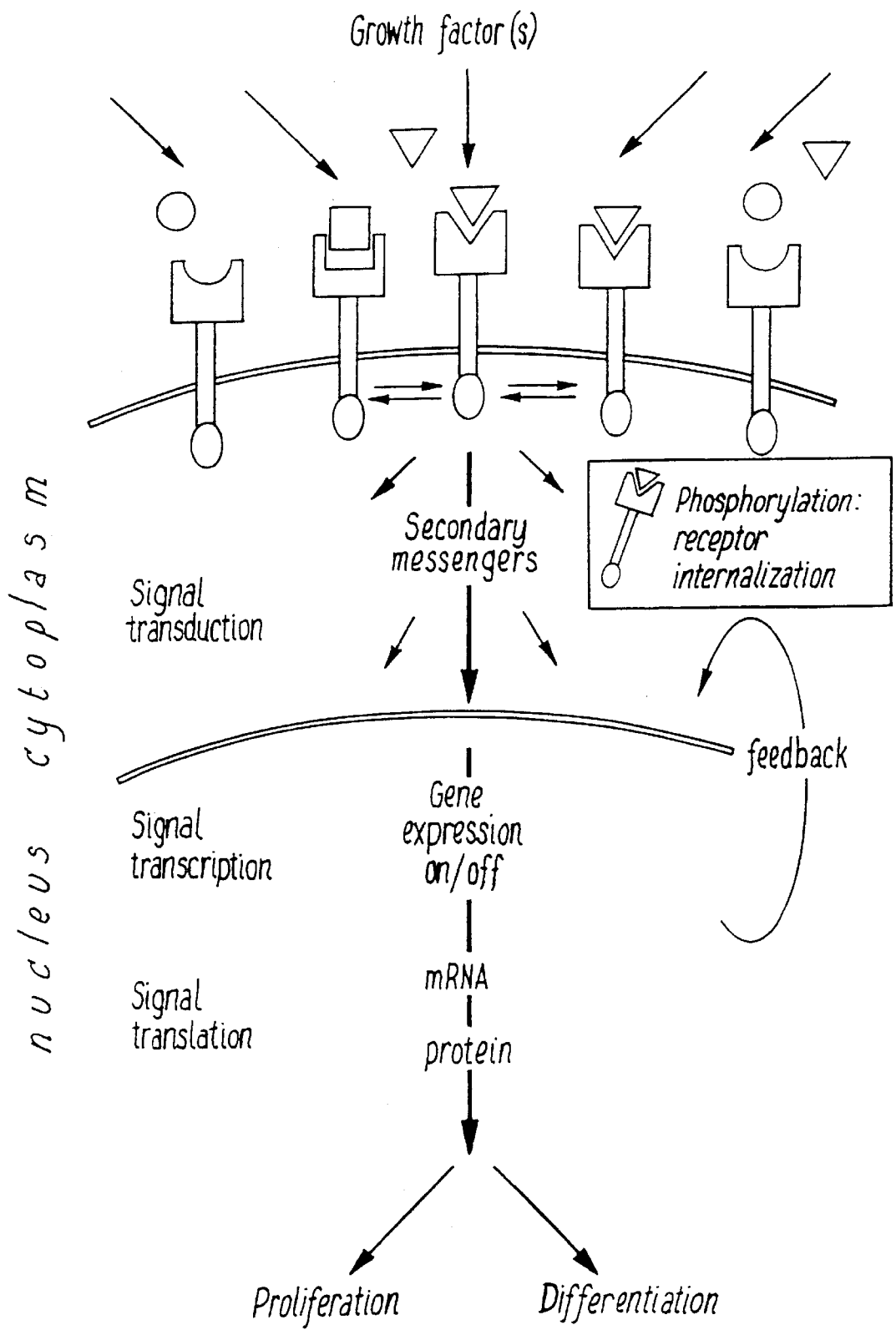

FIG. 10 is a schematic representation of growth factor effects.

Figure 11:
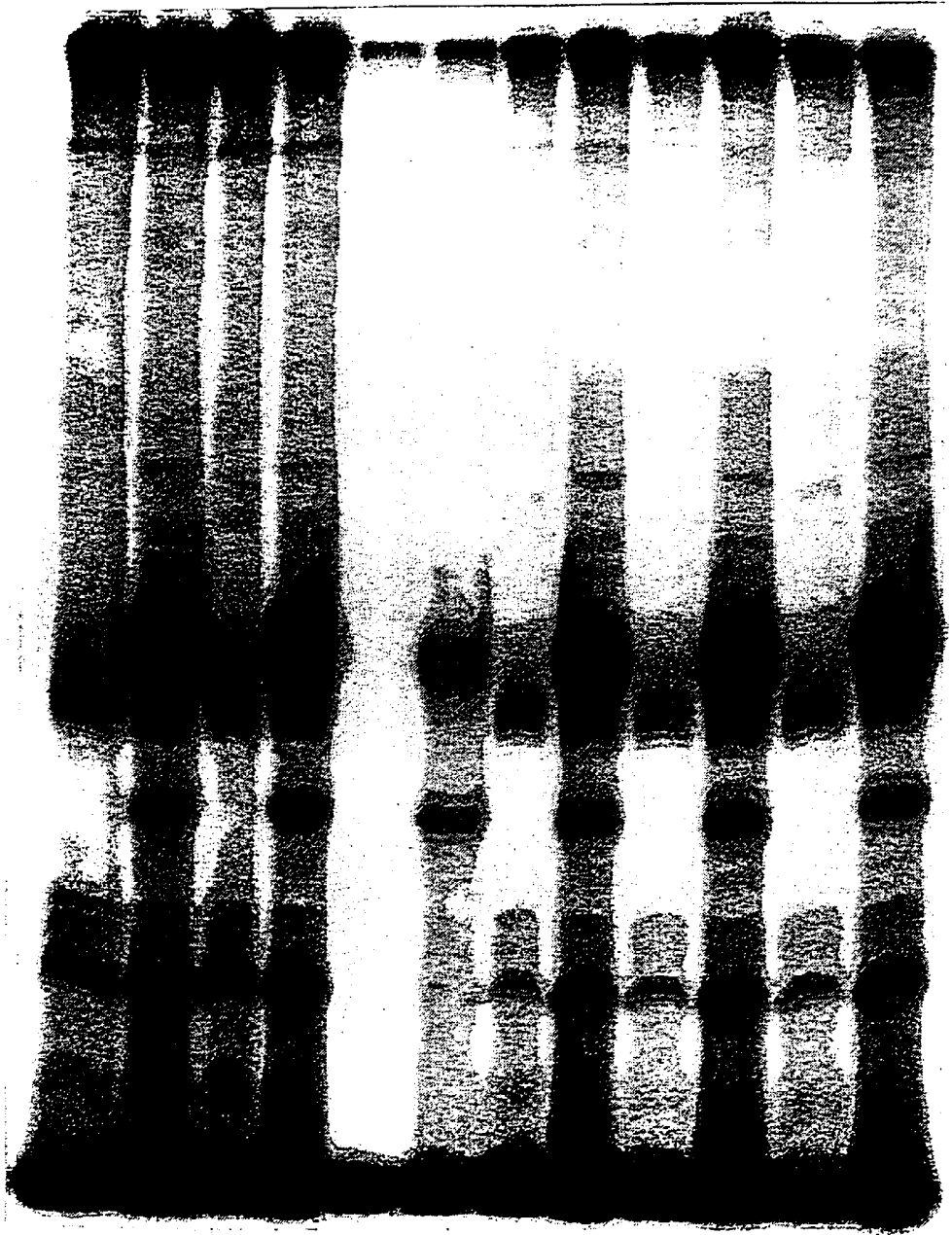

FIG. 11 shows the effects of tyrosine kinase inhibitors Tyrphostin 1, 25, B42, B44 and B46 on the effects of colostrum on phosphorylation of microvillar membrane proteins. C=control; Col=colostrum.

Figure 12:
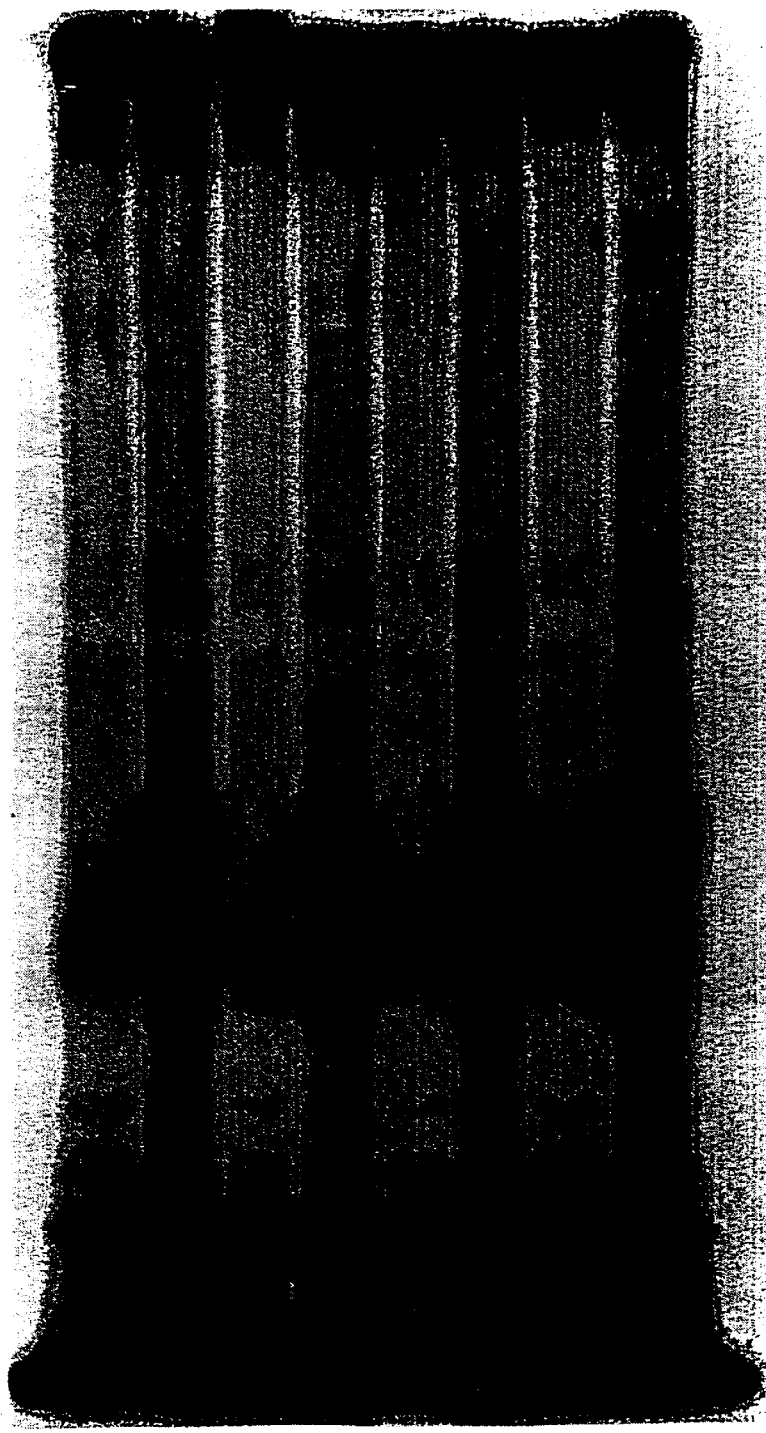

FIG. 12 shows the effects of tyrosine kinase inhibitors Tyrphostin B46, B48, B50 and B56 on the effects of colostrum on phosphorylation of microvillar membrane proteins. C=control; Col=colostrum.

Figure 13:
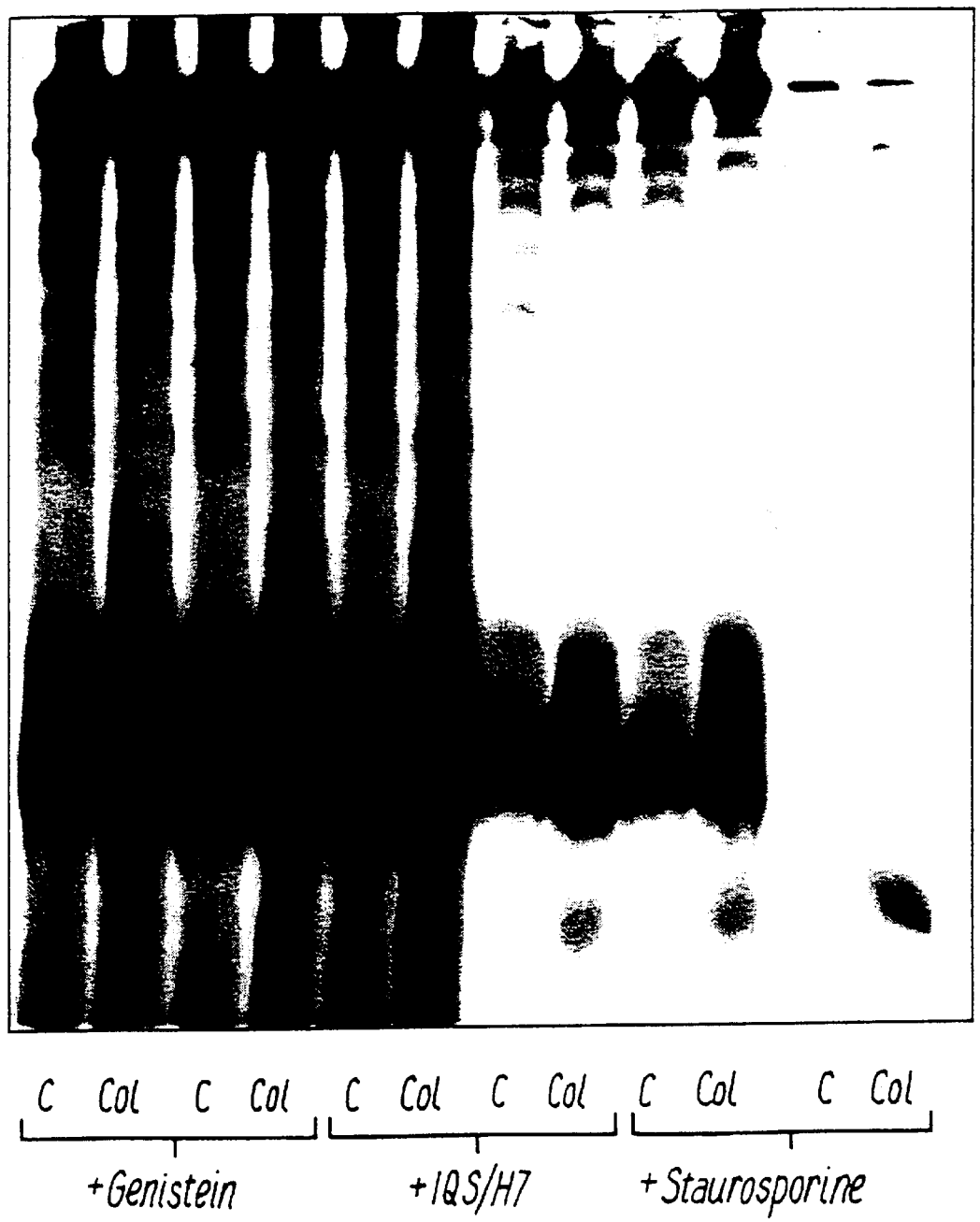

FIG. 13 shows the effects of Genistein, H7 and Staurosporine on the effects of colostrum on phosphorylation of microvillar membrane proteins. C=control; Col=colostrum.

FIG. 14 is a schematic representation of Ras protein activation for active and inactive receptors.

Figure 15:
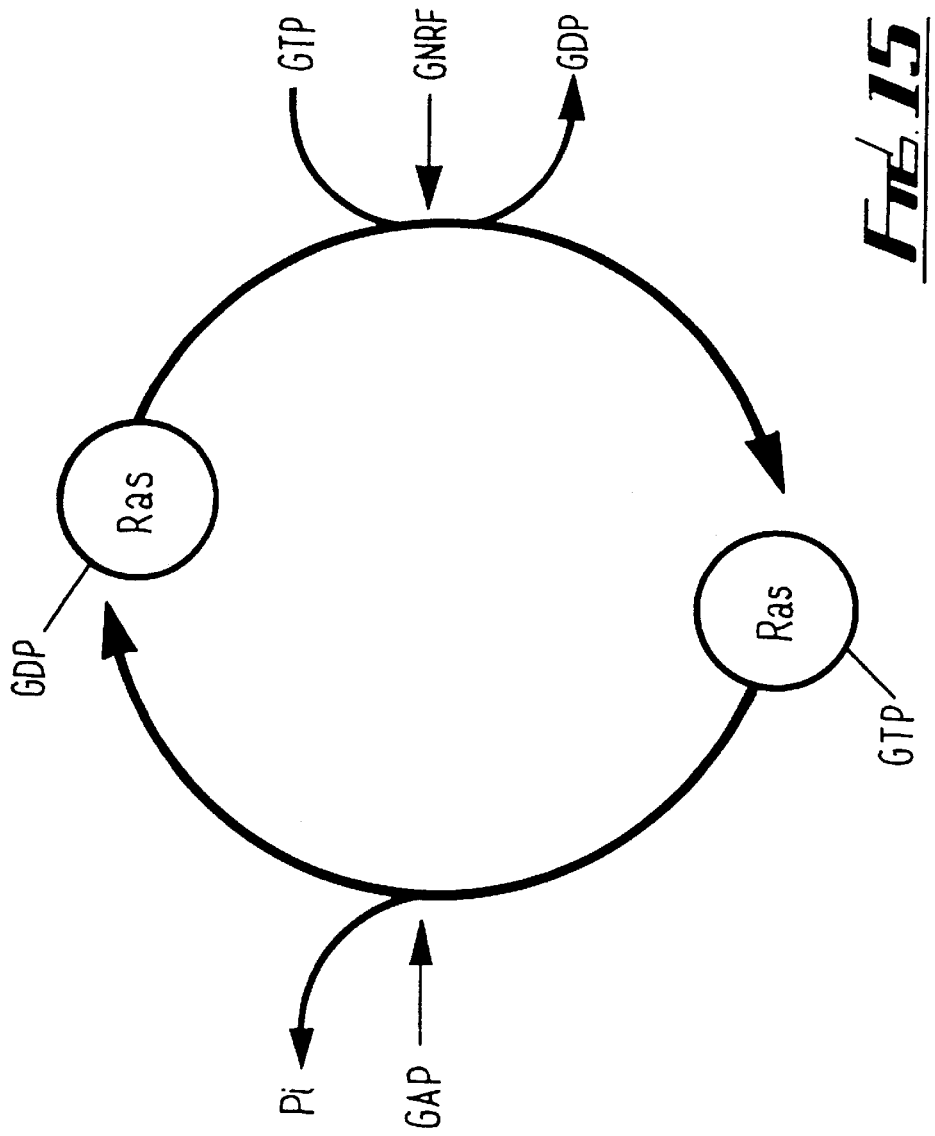

FIG. 15 shows the regulation of Ras protein schematically.

Figure 16:
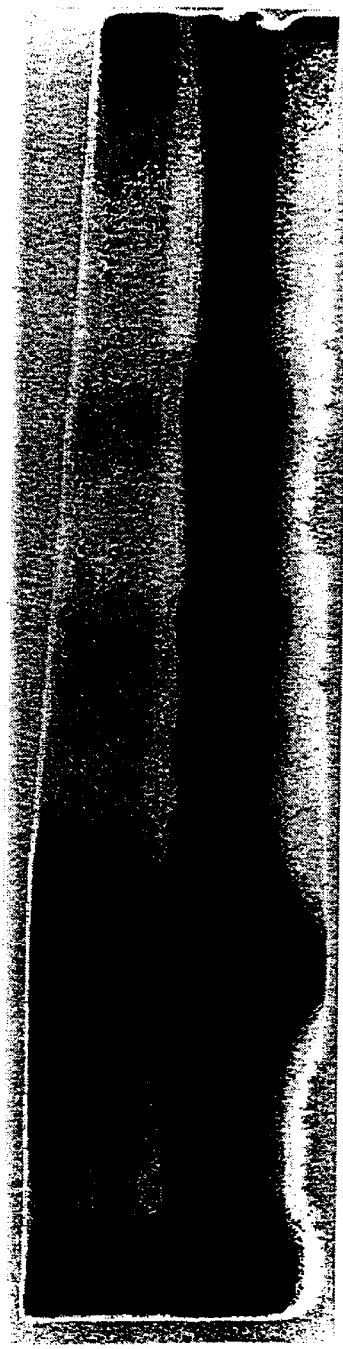

FIG. 16 shows the immunopurification of GAP from the colostrum phosphorylated microvillar membrane proteins of newborn pigs.

Figure 17:

FIG. 17 shows the purification of annexin and cytokeratin.

Figure 18:
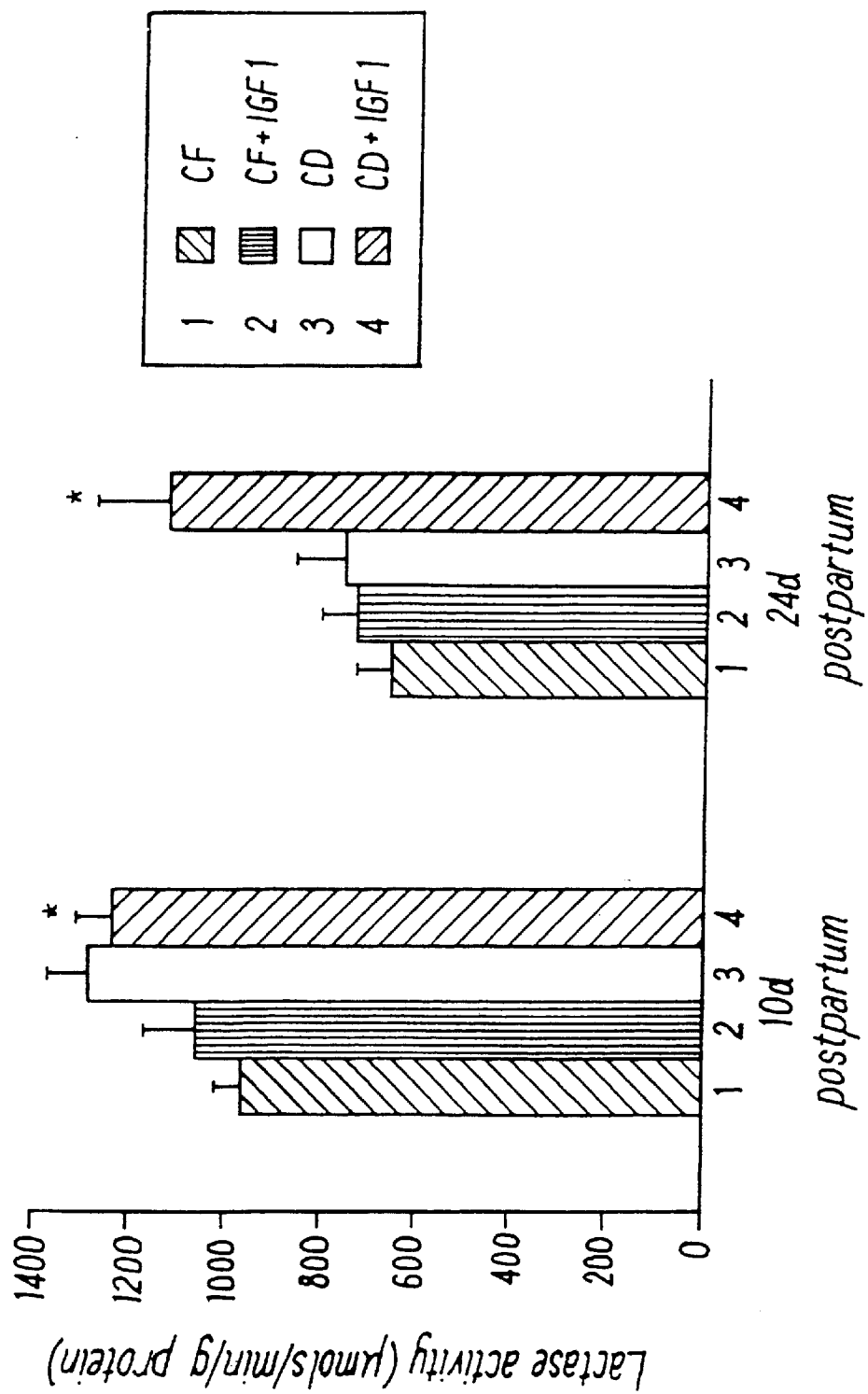

FIG. 18 shows the lactase activity of colostrum-deprived (CD) and colostrum-fed (CF) piglets with and without IGF-1 addition, at 10 days and 24 days postpartum.

Figure 19:
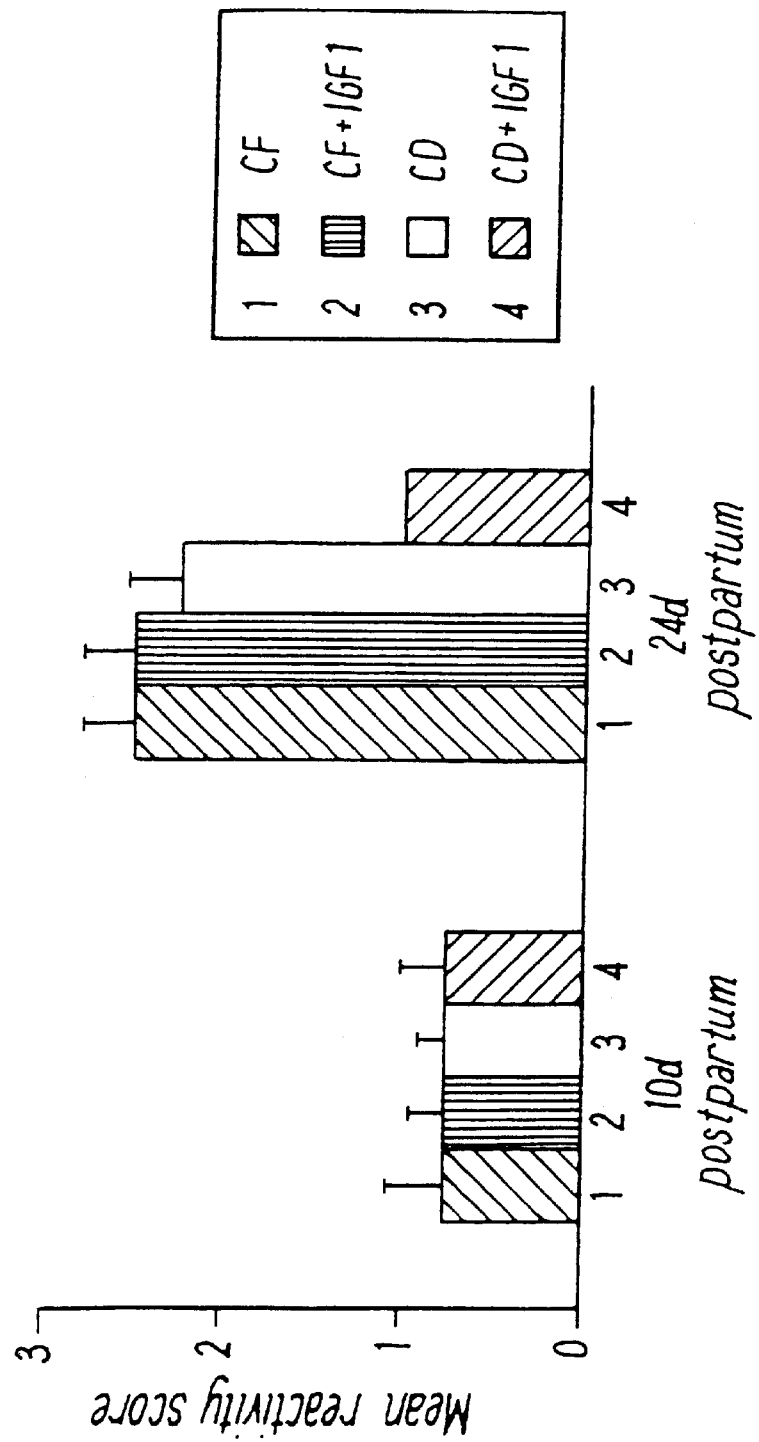

FIG. 19 shows the ($\alpha$2,3-sialylation of colostrum-deprived (CD) and colostrum-fed (CF) piglets with and without IGF-1 addition, at 10 days and 24 days postpartum.

Figure 20:
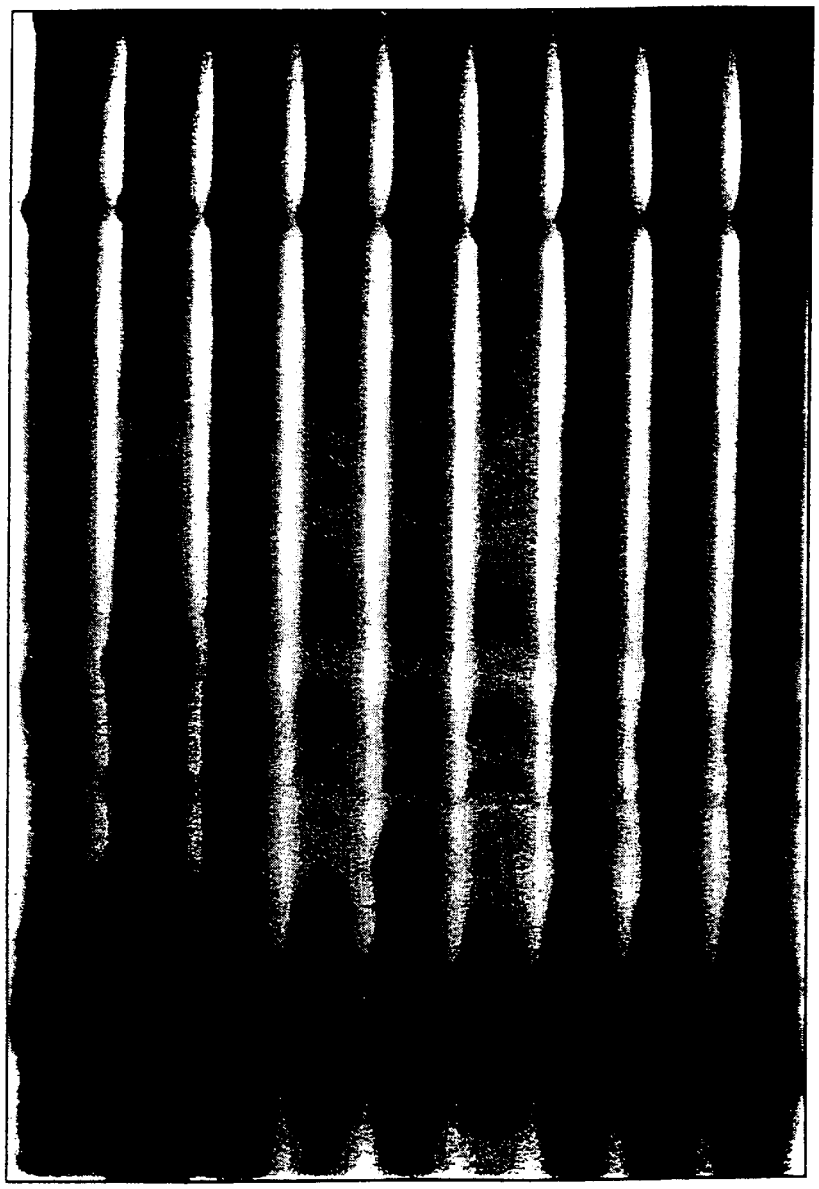

FIG. 20 illustrates a comparison of EGF, insulin, TGF with CDGF in the phosphorylation of microvillar membrane proteins.

Figure 21:
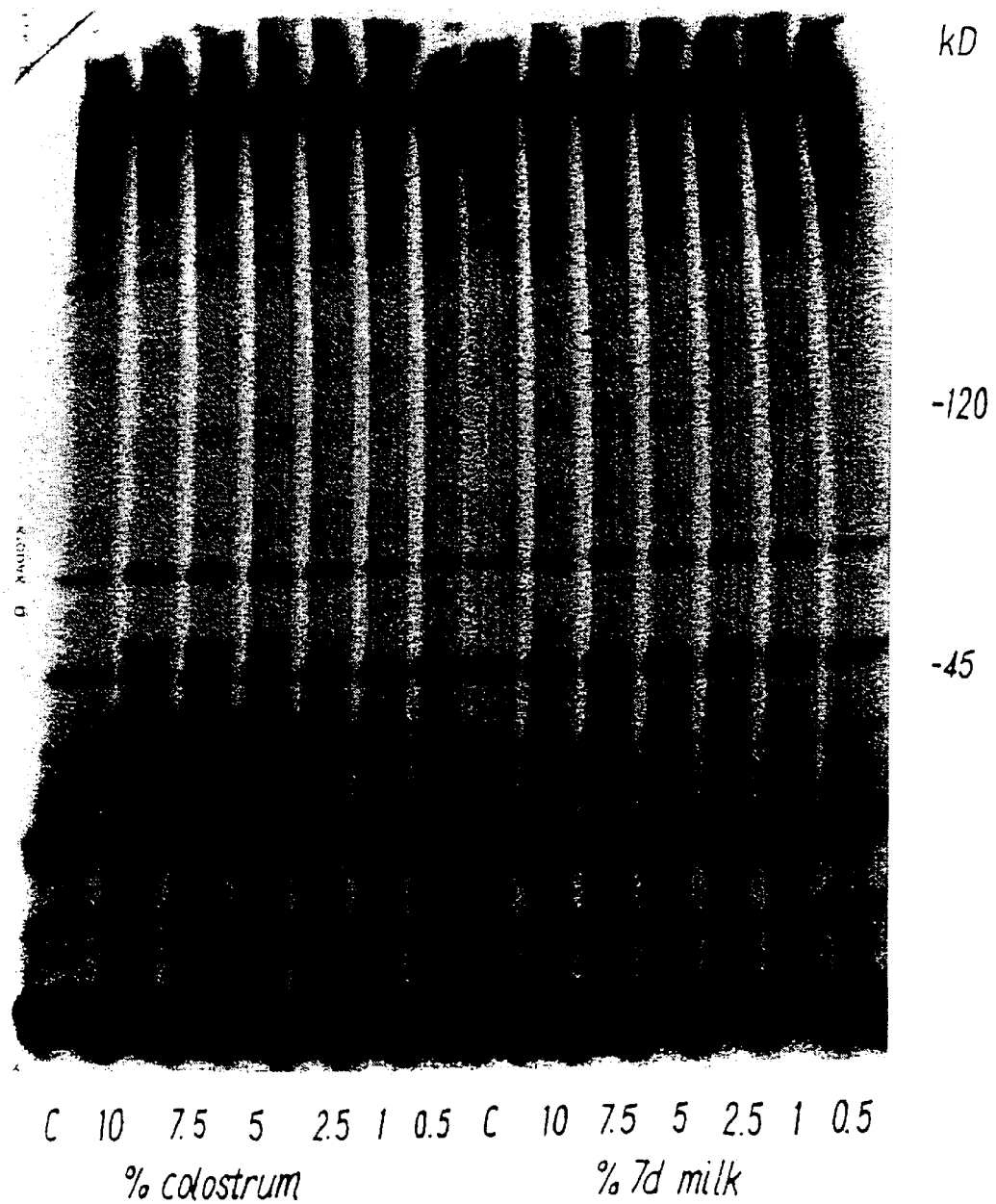

FIG. 21 shows the dose response of colostrum and milk produced at 7 days lactation in the phosphorylation of newborn microvillar membranes. C=control.

Figure 22A:
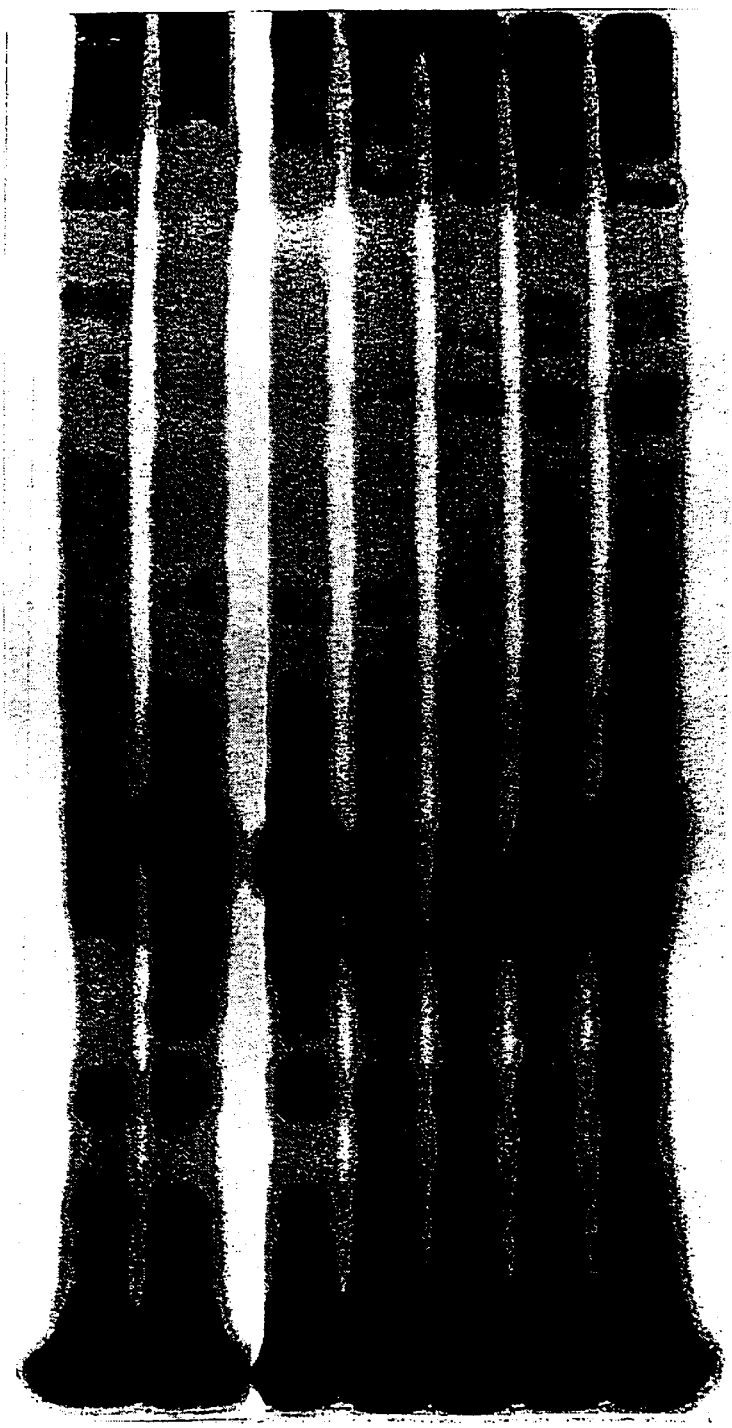

FIG. 22A shows the effect on colostrum phosphorylation of microvillar membrane proteins of heating to 100° C. for 10 minutes, of treatment with DTT, and of treatment with trypsin.

FIG. 22$b$ shows the effect of DTT/heat treatment on the purification of CDGF.

Figure 23:
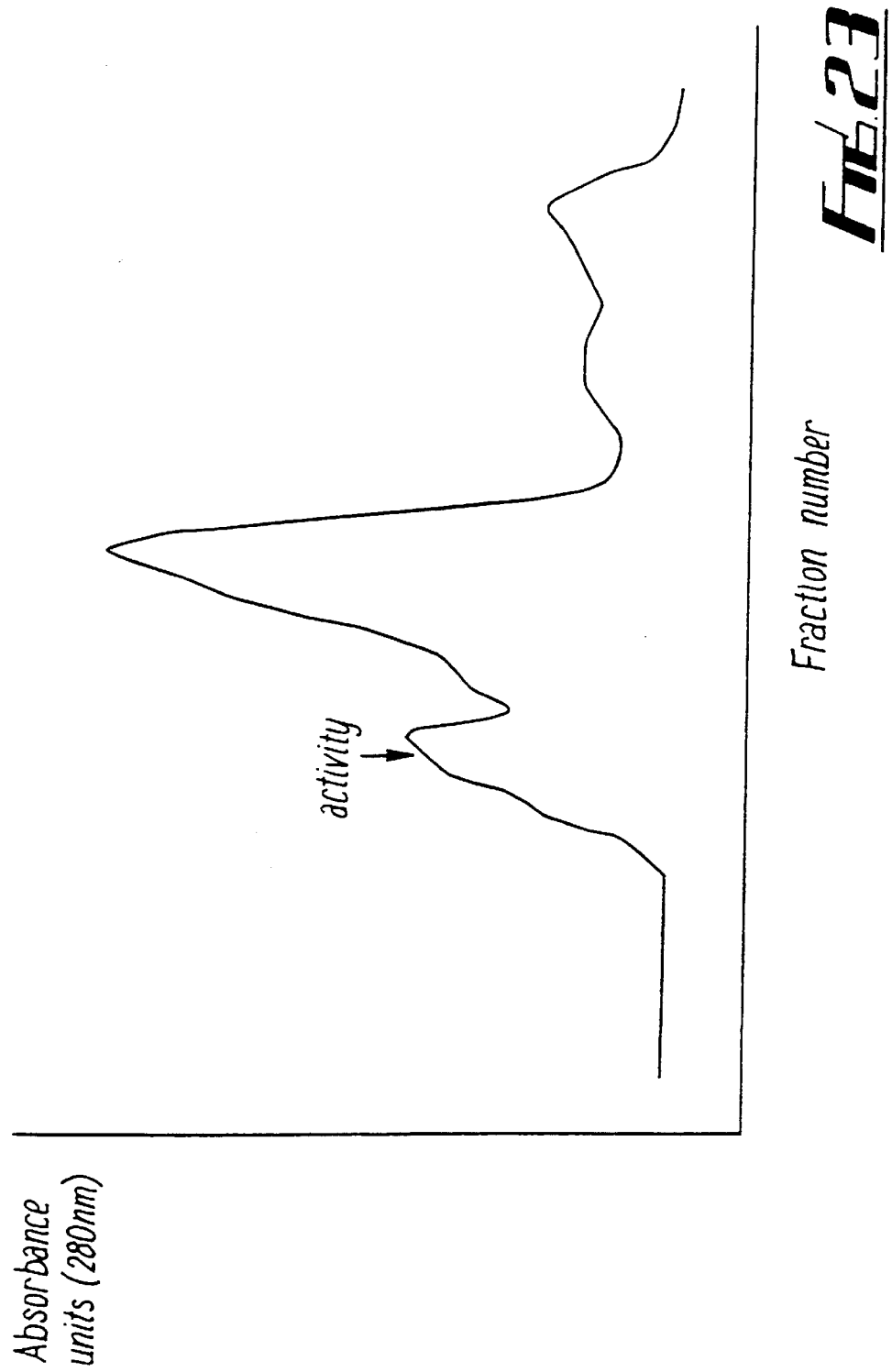

FIG. 23 presents the size exclusion chromatography gel filtration profile of colostrum.

Figure 24:
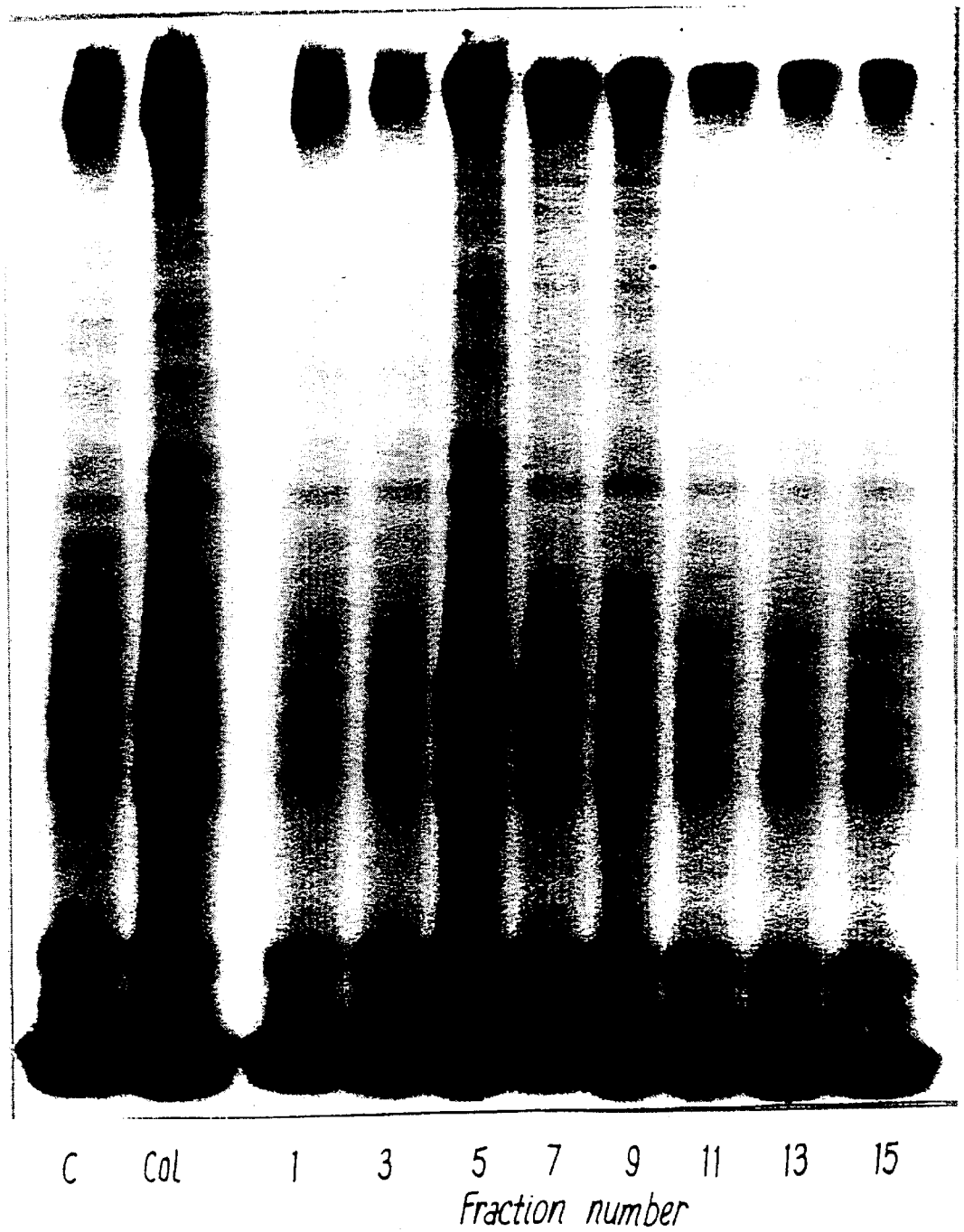

FIG. 24 shows the phosphorylation activity of the chromatography fractions.

Figure 25:
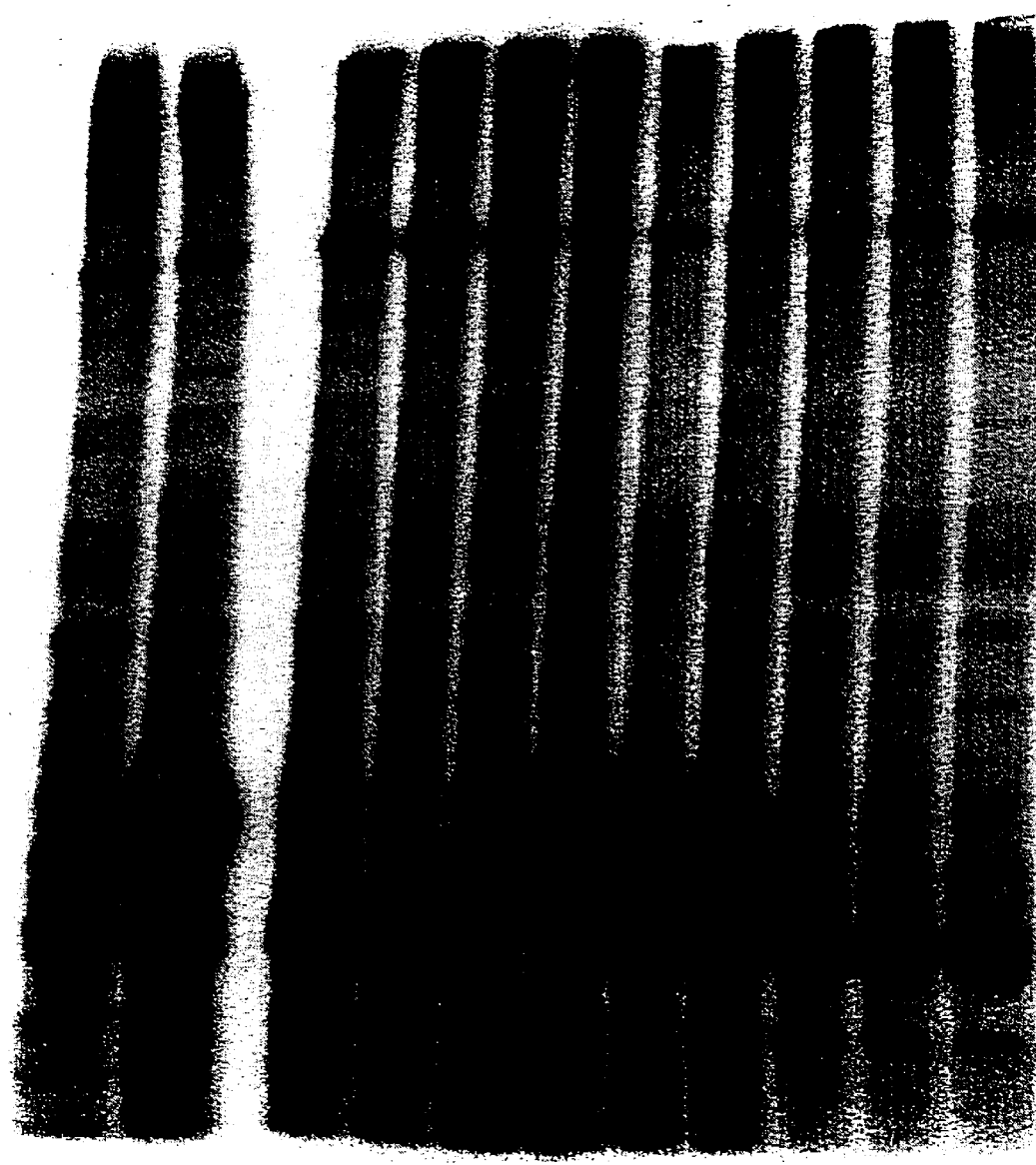

FIG. 25 shows the phosphorylation activity of fraction F5 purified by reverse phase chromatography with different % ACN for elution.

Figure 26:
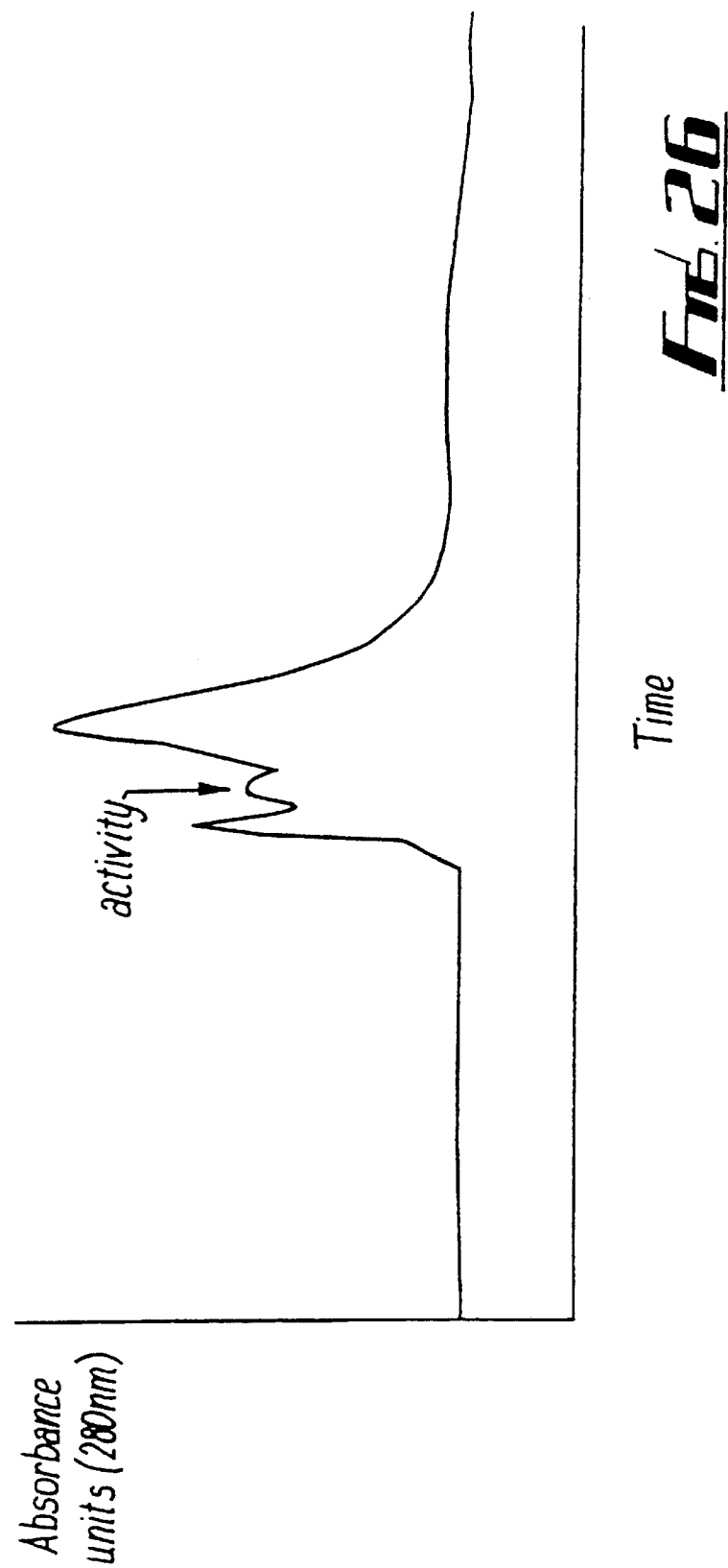

FIG. 26 shows the HPLC profile of fraction F5 in the presence of guanidine hydrochloride.

Figure 27:
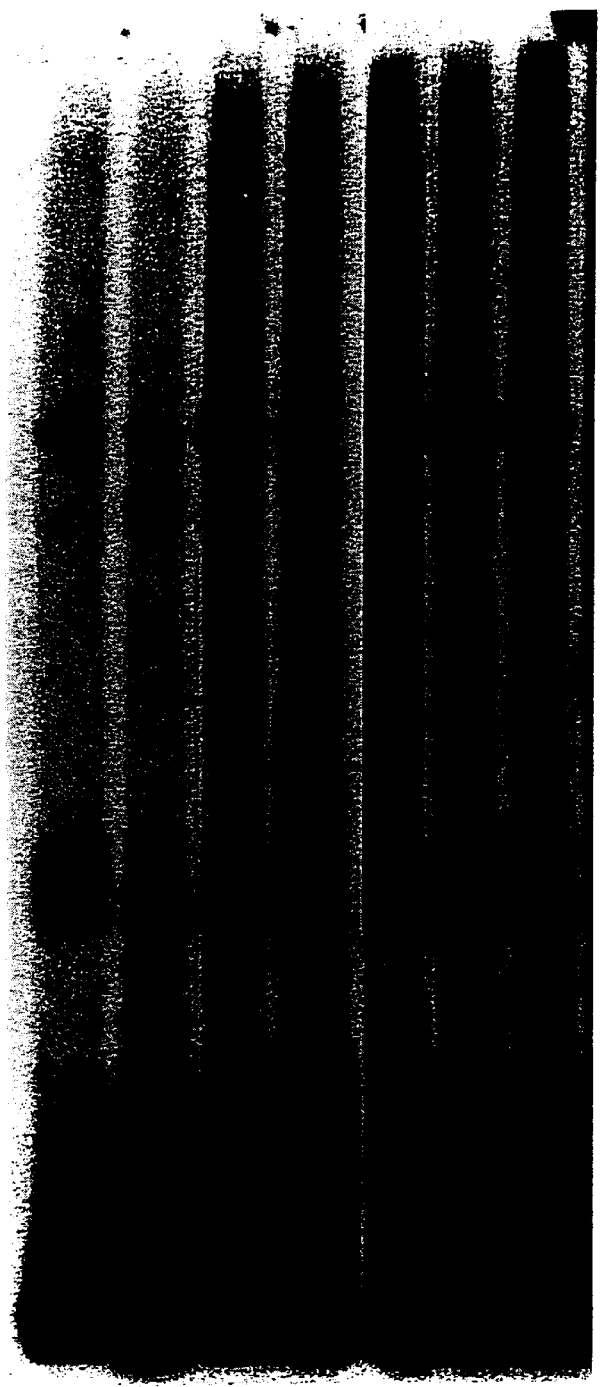

FIG. 27 shows the phosphorylation activity of the HPLC fractions.

Figure 28:
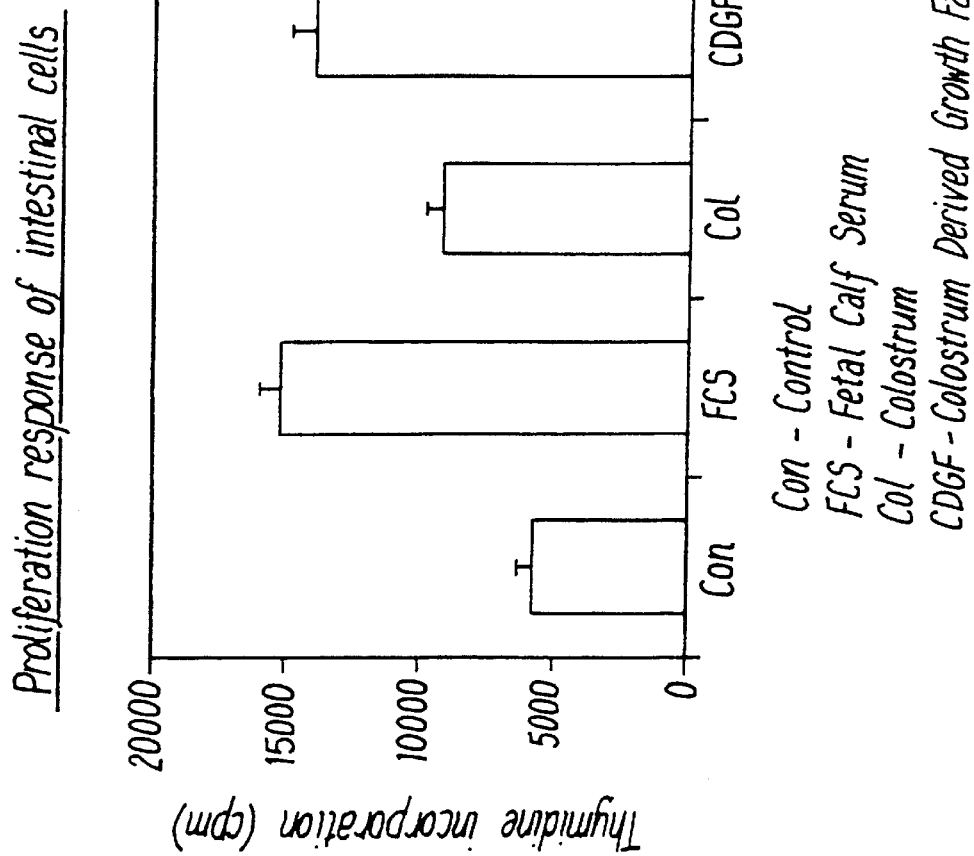

FIG. 28 shows the effect of colostrum and CDGF on rat intestinal crypt cells IEC 6.

Figure 29:
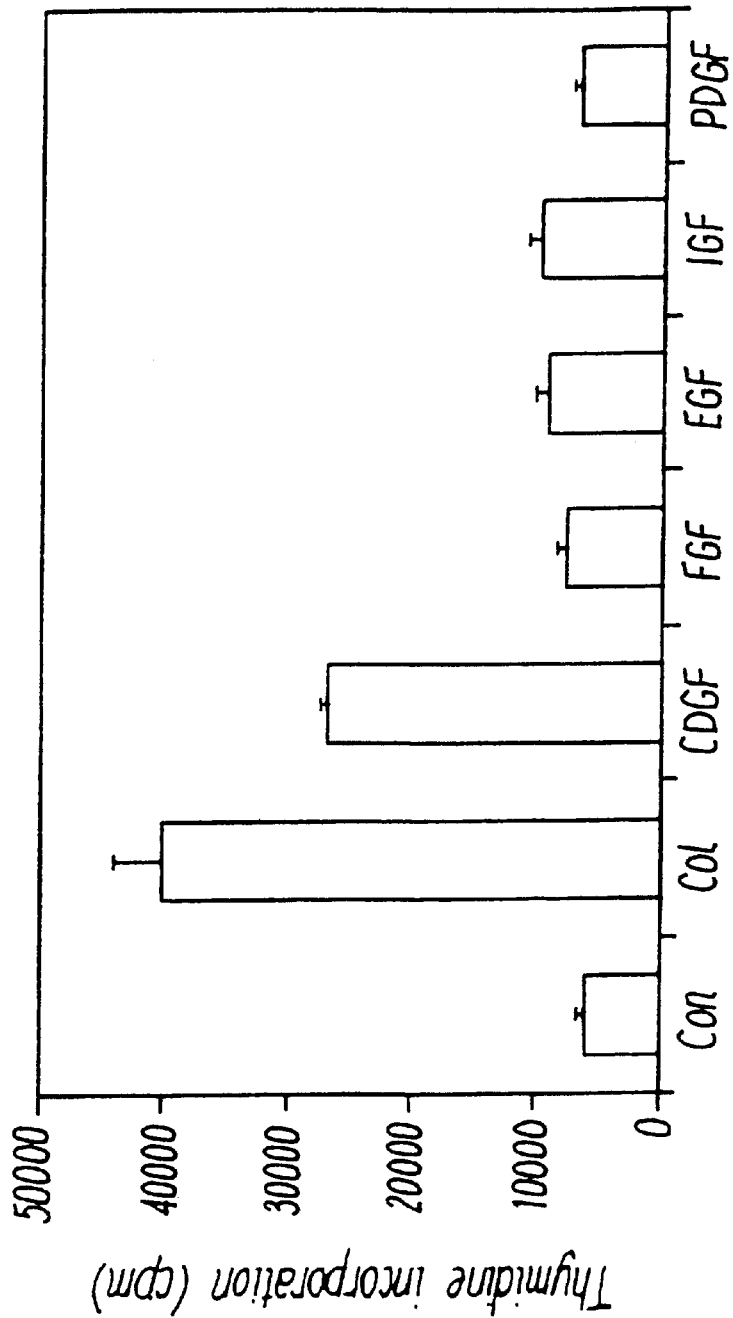

FIG. 29 is a comparison of the effects of colostrum and CDGF to the known growth factors FGF, EGF, IGF and PDGF on the proliferation of IEC 6 cells.

Figure 30:
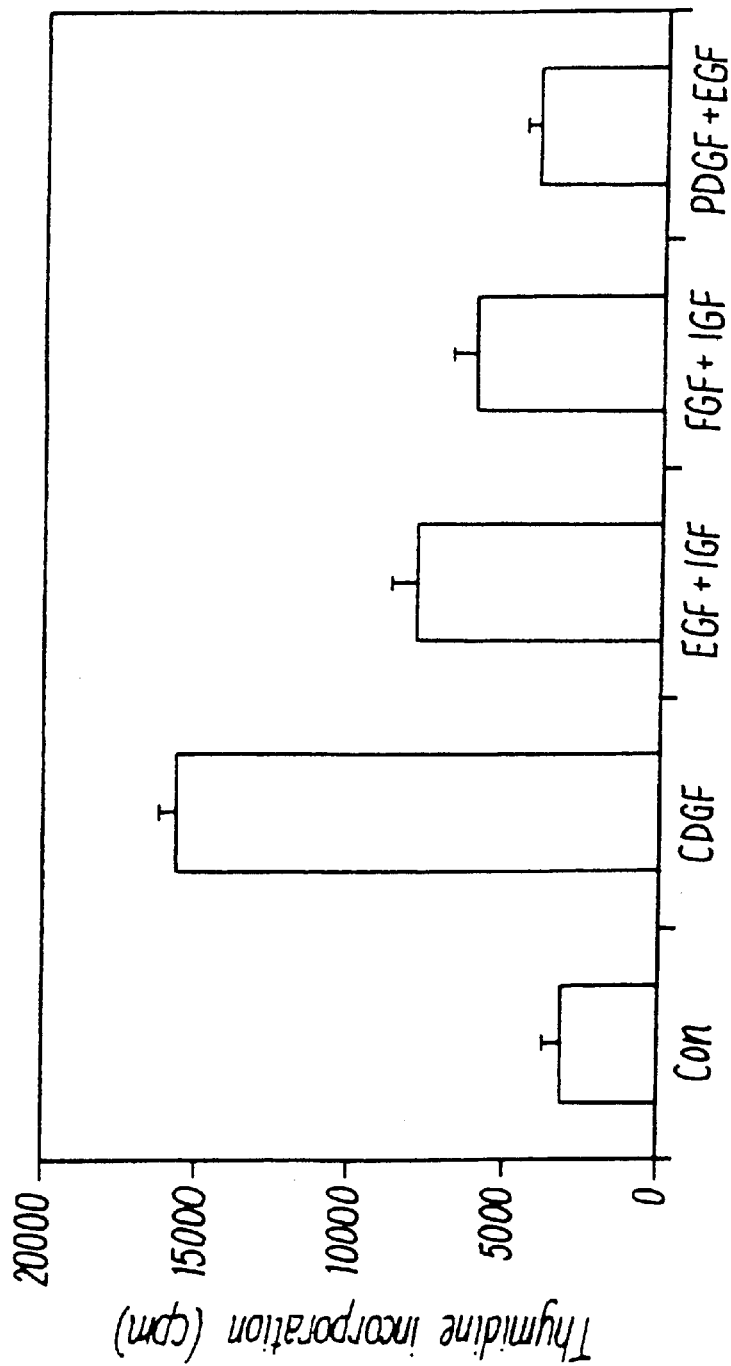

FIG. 30 is a comparison of the effect of colostrum and CDGF to combinations of the known growth factors FGF, EGF, IGF and PDGF on the proliferation of IEC 6 cells.

Figure 31:
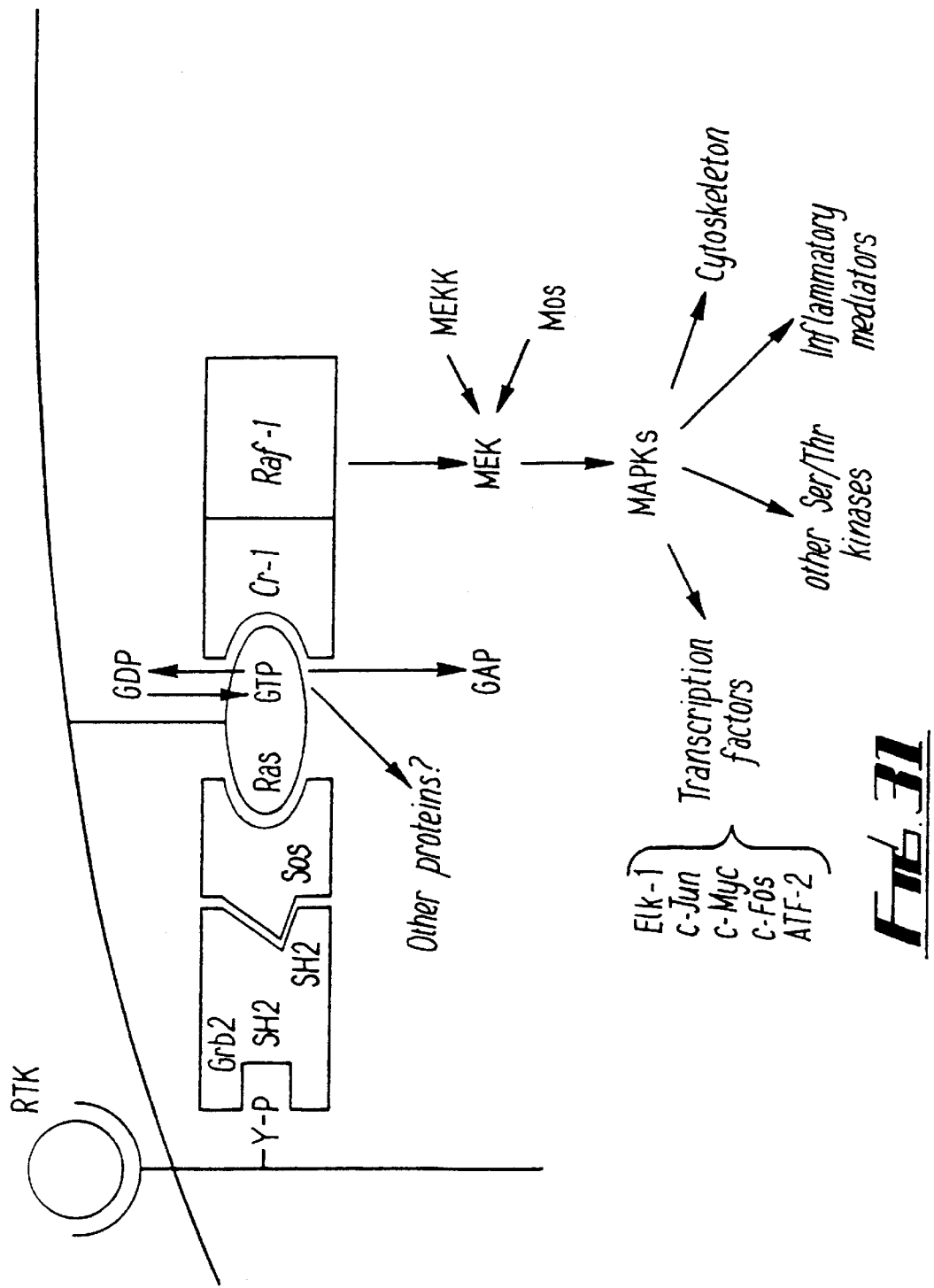

FIG. 31 is a schematic diagram of the involvement of the c-myc and Fos genes in the Ras pathway.

EXAMPLE 1

Identification and Purification of a Biologically Active Growth Factor Derived From Porcine Colostrum Introduction It is now a well established fact that ingestion of colostrum promotes protein synthesis, protein accretion and the growth of intestinal and peripheral tissues including skeletal muscle and liver. In addition, significant effects of colostrum on the differentiation of intestinal epithelia have been demonstrated. There has been much speculation concerning the biological nature of factors in colostrum which trigger these effects. Mammary secretions are known to provide a rich source of polypeptide growth factors which have a trophic (growth promoting) action and therefore represent very likely candidates. Support for this hypothesis stems from research conducted during the last 10 years which underscores the central importance of peptide growth factors in the control of intestinal epithelial cell division and differentiation. Compositional changes in growth factors have been reported during lactation in both human and porcine milk. Maximal mitogenic activity is observed during the first weeks of lactation and progressively decline thereafter. These changes are considered to be physiologically relevant in modulating the maturation of the intestine. The data presented herein describes the biological effect of porcine colostrum on intestinal differentiation and the identification and isolation of a potent potentially novel growth factor. The biologically activity of the latter is also described.

Research Strategy

We have utilised several approaches to identify bioactive colostral constituents. Initially, a whole animal approach was used to demonstrate the efficacy of whole colostrum in promoting intestinal protein synthesis and enterocyte differentiation. However, more recently in vitro strategies have been adopted to identify, isolate and characterise a potent growth factor and also to define the cellular and molecular actions of a colostrum-derived growth factor (CDGF).

In vivo effect of colostrum on intestinal maturation

During the neonatal period the intestine undergoes extensive structural and cytochemical remodelling. For example, lactase, the major intestinal disaccharidase responsible for the hydrolysis of the primary carbohydrate in milk declines dramatically during the postnatal period. Hence measurement of enzyme expression in the intestinal epithelium has been routinely employed to investigate intestinal development and adaptation. In addition, distinct age related changes in the terminal glycosylation of both secretory and membrane glycoconjugates occur. The cytochemical data presented in previous publications (see Kelly and King, 1991 *Histochemical Journal.;* 23: 55–60.) have demonstrated that histoblood group antigens are very sensitive intestinal differentiation markers. To demonstrate that colostrum and early milk could influence intestinal maturation, several in vivo experiments were undertaken. The details of one experiment describing the effect of colostrum feeding on the expression of lactase and intestinal glycosylation is presented.

Experimental Protocol Colostrum Collection

Lactating sows received a single injection of oxytocin to stimulate milk letdown. Colostrum samples were obtained by manual expression and stored frozen in sterile containers. On the initial days of the experiments the colostrum was thawed and pooled to ensure homogeneity.

Animals

Figure 1:
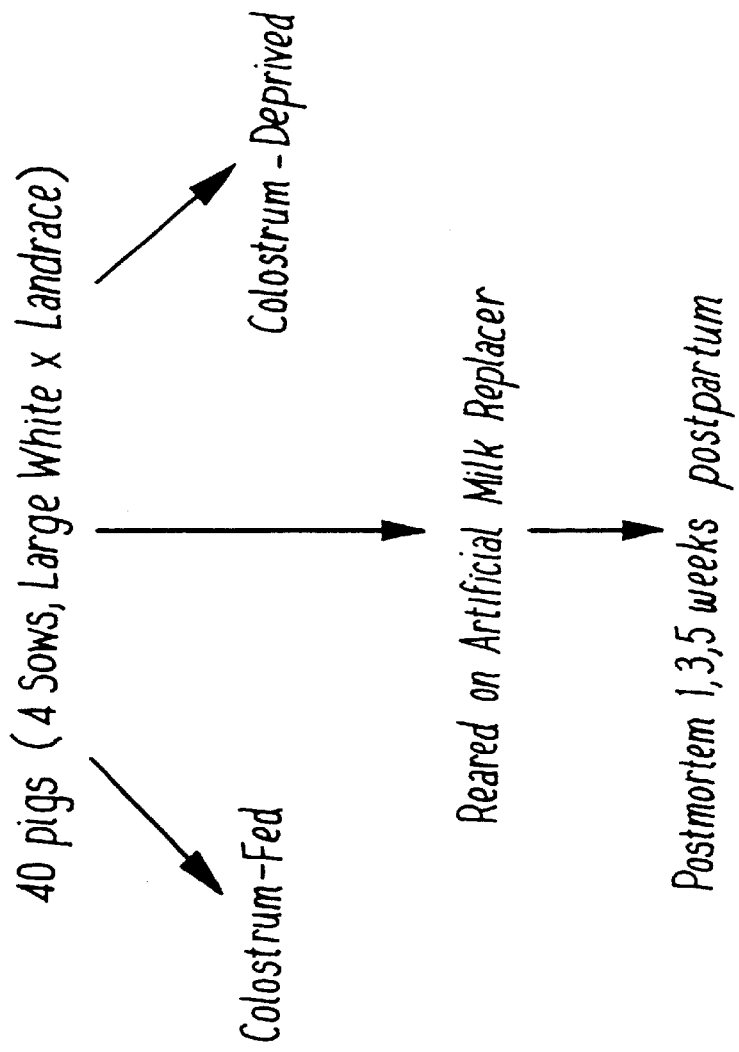
FIG. 1 is a schematic representation of the experimental protocol for animal handling.

The progeny for the trials were derived from 5 sows (Large White×Landrace). Using a combination of concurrent matings and pharmacological manipulations all sows were farrowed within 24 hours. Six piglets from each sow were caught at birth and housed in sterile incubators. Half the piglets from each litter were gavaged with colostrum or a commercial substitute (FIG. 1). The latter feed preparation was assessed in cell culture systems and found to be devoid of growth factor activity. Five piglets from each treatment were killed at 1, 3 and 5 weeks postpartum. Intestinal tissue was obtained under anaesthesia.

Results

Figure 2:
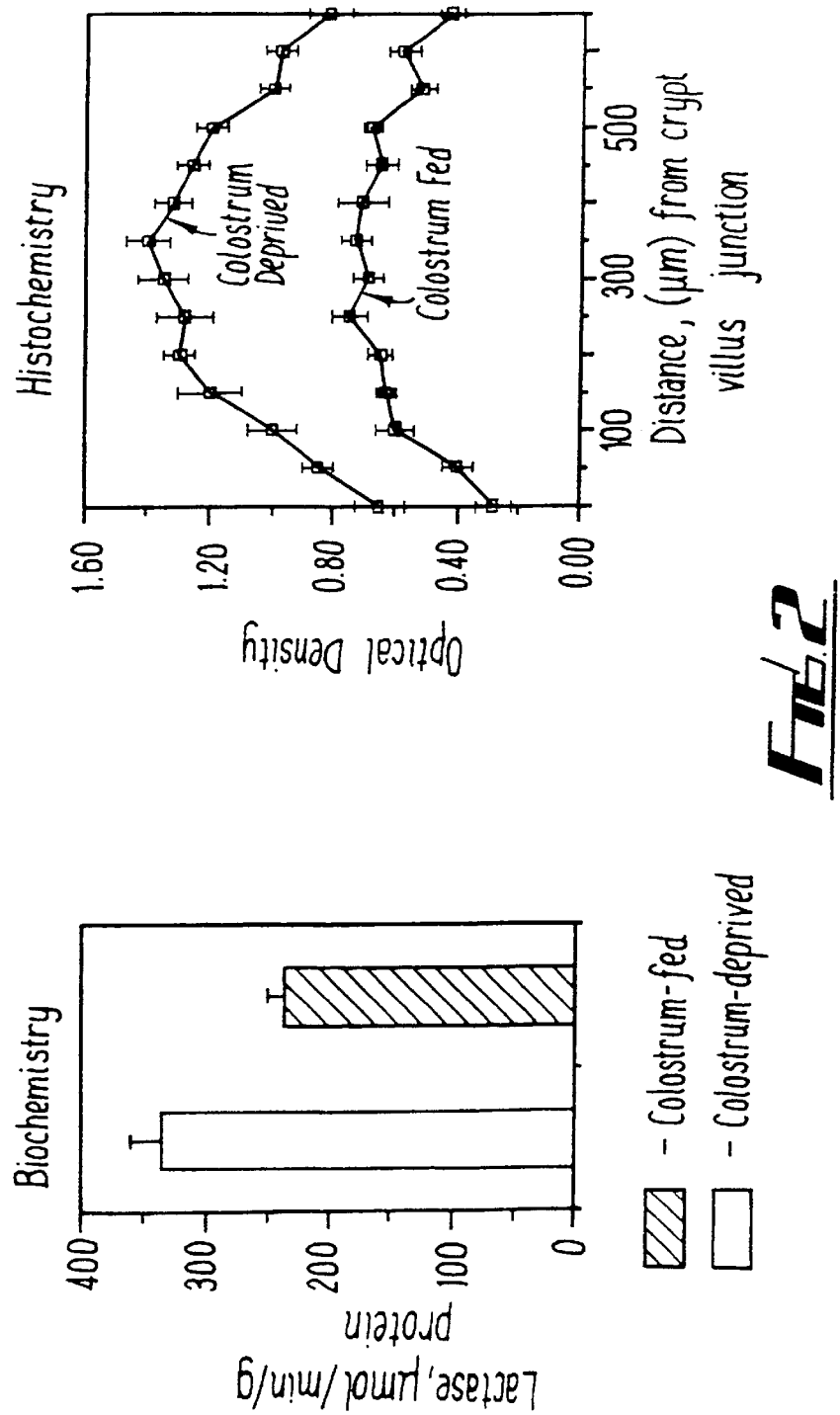
FIG. 2 shows the intestinal lactase and distance from villus crypt junction in colostrum fed and colostrum deprived piglets 1 week postpartum.

At 1 week postpartum intestinal lactase (specific activity and histochemically determined villus/crypt activity) declined significantly in colostrum-fed piglets compared to substitute-fed animals (FIG. 2). Similar data has recently been described by Burrin et al. *Journal of Nutrition* 124 2350–2357 (1994). At 3 and 5 weeks postpartum the activity of another enzyme, sucrase, was increased in colostrum-fed piglets compared with their colostrum-deprived littermates (Kelly et al *Biology of the Neonate* 64, 235–244 1993).

Figure 3:
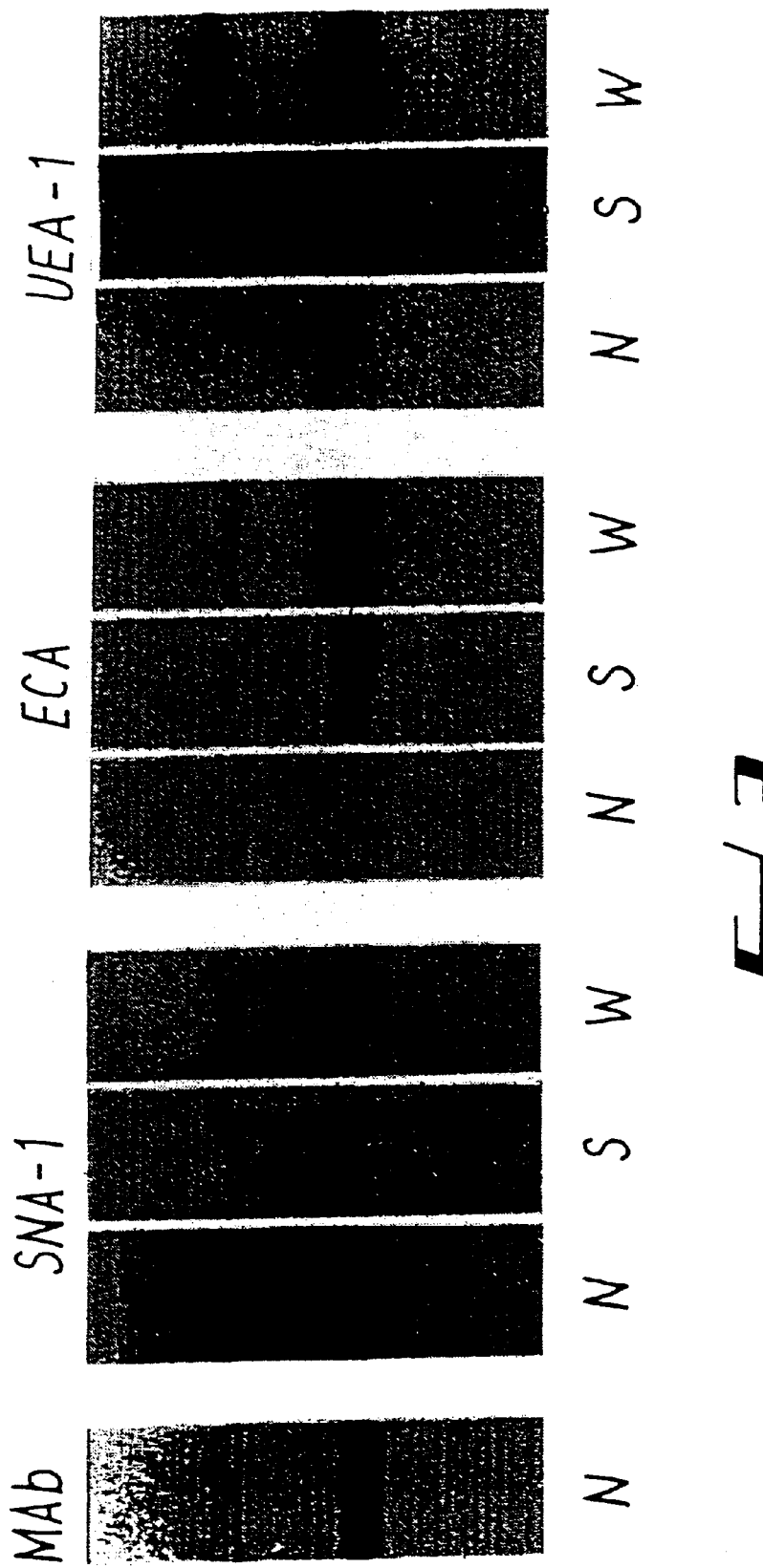
FIG. 3 shows glycoforms for lactase in newborn (N), suckled (S) and weaned (W) piglets.
Figure 4:
FIG. 4 shows the increase in 2,6 sialylation in colostrum fed piglets at week 3.

A progressive change from α2,6-sialylation to α1,2-fucosylation and α2,3-sialylation expression on intestinal glycoconjugates occurs during postnatal development in pigs. This temporal event is demonstrated for the enzyme lactase (FIG. 3). Significantly the loss α2,6-sialylation at week 1 postpartum and the ontogenic increase in α2,3-sialylation at week 3 is more advanced in colostrum-fed piglets (FIG. 4) (Kelly et al. 1993, supra). In a related study, prolonging the intake of early milk was found also to result in precocious decline in intestinal lactase and expression of histo-blood group AO antigens on the intestinal membranes (Kelly et al. 1991 supra and Kelly et al. 1991 Gut; 32:386–392).

Conclusion

Colostrum ingestion in newborn pigs resulted in a significant proliferative response in the small intestine accompanied by a dramatic decline in lactase These early responses were correlated with postnatal changes in the sialylation of intestinal membranes. Both this and previous studies confirm that colostrum and early milk contain factors which regulate intestinal maturation.

EXAMPLE 2

Identification of Bioactive Factors in Colostrum

The current consensus opinion is that nonnutrient components of colostrum are responsible for the growth promoting and maturational effects of colostrum. The identity and functions of many of the bioactive constituents of colostrum and milk are currently unknown and remain to be elucidated. Observations over the past twenty years have underscored the central importance of peptide growth factors in the regulation of cellular function. Colostrum is an abundant source of bioactive hormones and growth factors (FIG. 5) many of which have been shown when administered in isolation to influence intestinal growth, differentiation, the development of the immune system and enteroendocrine system. Growth factors can be defined as proteins (5 kD–80 kD) that possess growth modulating bioactivity. However, their biological actions also include modulation of cellular phenotype. To exert biological effects growth factors must interact with specific high-affinity membrane bound receptors and activate appropriate signal transduction/second messenger cascades. Receptor enzymes (tyrosine kinase) and G-protein coupled receptors form the transduction elements located in plasma membranes. This basic mechanism of ligand/receptor activation was utilised to develop an in vitro second messenger bioassay to screen colostrum and colostrum fractions for biological activity.

Phosphorylation Bioassay

Microvillar Membrane

Preparation: Intestinal brush border/ microvillar membrane (MVM) vesicles were prepared from mucosal scrapings of fresh or frozen tissue from newborn, suckled and weaned pigs. Sections of the intestinal tube were opened longitudinally on an ice pack and the mucosae removed by gentle scraping with the edge of a microscope slide. The tissue was dispersed in 3 volumes of buffer (buffer A) consisting of 2 mM Tris-HCl, 50 mM mannitol, pH 7.4 (containing Leupeptin, 1 $\mu$M; pepstatin, 1 $\mu$M; PMSF, 0.2 mM; di-sodium EDTA, 0.1 mM; antipain, 27 $\mu$g/ml) using a loose-fitting glass-glass homogeniser and any adventitious connective tissue removed by centrifugation at 200 g for 3 minutes. The supernatant was diluted with 5 volumes of buffer A and the suspension was further homogenised by 10–15 passes at 1000 rpm in a teflon glass homogeniser. Solid $MgCl_2$was added to 10 mM and the suspension allowed to stand in ice for 20 minutes before being centrifuge at low speed (300 g for 15 mins). Crude BBMv were pelleted from the supernatant by further centrifugation at 27,000 g for 30 minutes and the final preparation obtained after two cycles of gentle resuspension in buffer A followed by centrifugation at 27,000 g for 30 minutes.

Phosphorylation Bioassay

MVMv preparations were solubilised in 20 mM Hepes, 5 mM $MnCl_2$, 4 mM NaF, 100 $\mu$M $Na_3VO_4$, 10 mM β-glycerophosphate 1 $\mu$g/ml leupeptin, 25 $\mu$g/ml Trypsin inhibitor, 25 KIU/ml Aprotinin, 0.1 M PMSF, 0.0 5% bacitracin (Buffer B) containing 2% Triton X-100 for 3 hours at 4° C. Membrane soluble proteins were obtained following centrifugation at 27,000 g for 30 minutes. Solubilised MVMv were diluted with Buffer B to a protein concentration of 3 mg/ml. 30 $\mu$l of solubilised membranes were incubated with 5 $\mu$l of 1:10 dilution of defatted acellular colostrum, colostrum fractions, or nanomolar concentrations of known growth factors and 5 µl Buffer B at ambient temperature for 10 minutes and then on ice for a further 15 minutes (FIG. 6). Phosphorylation was initiated by the addition of 10 µl of 20 µM γ-$^{32}$P-ATP (20 µCi) prepared in Buffer B. The reaction was terminated after 15 minutes at 4° C. using 3× Laemmli buffer and boiling for 10 minutes at 100° C. Phosphorylated MVMv were analysed on 7.5% SDS polyacrylamide gels under reducing conditions. Autoradiograms of dried gels were obtained with X-Omat AR film.

Experimental Results

Phosphorylation of Microvillar Membrane Proteins in Response to Colostrum and IGF-1

To validate this in vitro assay it was necessary to demonstrate the efficacy of known growth factors. Previous data from our laboratory had demonstrated the presence of specific receptors for the peptide growth factors IGF-1 in the intestine of neonatal pigs. These receptors were found to be localised to musculature, lamina propria and to the mucosa of the intestine. Detailed cellular analyses revealed a population of apical or microvillar membrane IGF-1 receptors. Using the phosphorylation assay we successfully demonstrated enhanced incorporation of radioactive phosphorus into a number of MVM proteins in response to IGF-1 and defatted acellular colostrum (FIG. 7). IGF-1 was found to stimulate the 97 kD subunit of the IGF receptor in addition to other membrane substrates. Colostral whey was found to stimulate the phosphorylation of several membrane proteins in the molecular weight range 29–200 kD. A prominent feature is the hyperphosphorylation which can be observed in the molecular range 29–45 kD.

Phosphorylation of Newborn, Suckled and Weaned Microvillar Membranes

Newborn, suckled and weaned membrane preparations produced similar qualitative responses to defatted colostrum (FIG. 8). However, on an equivalent membrane protein base MVM proteins from suckled animals appear to be stimulated to a greater extent. The order of potency being suckled, weaned and then newborn. This temporal response is likely to reflect quantitative differences in membrane receptor expression during development. The intestinal membrane receptor can be significantly enriched following wheat-germ agglutinin affinity purification. Briefly solubilised MVM were applied to "WGA-Sepharose" affinity columns (2 ml of supernatant/ml of resin bed) which had been previously equilibrated with 20 mM Hepes, 10 mM MgCl$_2$, 0.1% Triton x-100, pH 7.6. The columns were incubated end over end for 6 hours at 4° C. The resin was then washed with 100 ml with the above equilibration buffer including protease inhibitors. Bound glycoproteins were eluted in 500 µl fractions with the buffer containing 20 mM Hepes, 0.05% Triton X-100 and 0.3M N-acetyl-D-glucosamine. Fractions 1 to 8 were pooled and concentrated 10 fold using 30 kD filtrons (Filtron, UK). Phosphorylation of WGA-purified proteins was carried out as described above. The result (FIG. 9) illustrates significant enhancement of the phosphorylation of membrane proteins, in particular the hyperphosphorylated proteins and a 120 kD protein. This result provided some insight into the second messenger cascade which is activated by colostrum.

Activation of an Intestinal Membrane Tyrosine Kinase Receptor by Colostrum

As mentioned above there are two main membrane bound receptor classes namely tyrosine kinase receptors and G-protein coupled receptors. Many of the transmembrane receptors for peptide growth factors possess intrinsic tyrosine kinase activity which upon ligand binding induce autophosphorylation and phosphorylation of a number of membrane and cytosolic substrates (FIG. 10). Specific inhibitors were employed to ascertain the receptor class mediating the effects of colostrum. A series of organic compounds named tyrphostins derived from a benzylidenemalononitrile nucleus have been shown to inhibit receptor tyrosine kinase activities. The following inhibitors were tested Tyrphostin 1, 25, B42, B44, B46, B48, B50, B56 at concentrations ranging from nanomolar to micromolar (FIG. 11, 12). Genistein, staurosporine and H7 (FIG. 13) were also investigated. Genistein is an isoflavone compound and staurosporine a microbial alkaloid. Staurosporine inhibits tyrosine kinase but also effects protein kinase C (PKC). Membrane preparations were incubated overnight in the presence of the inhibitors and the phosphorylation assay carried out as described above. Tyrphostin 25, staurosporine and H7 significantly inhibited membrane protein phosphorylation indicating that the receptor is a tyrosine kinase receptor. PKC may also be involved.

Activation of RAS/GAP Phosphorylation by a Defatted Acellular Colostrum

Activation of Ras proteins is a key step in the biochemical pathways triggered by ligand-bound cell surface tyrosine kinase receptors. Equally it has been long established that Ras, a 21 kD GTP-binding protein, plays an important role in growth control. The activity of Ras is determined by whether it is occupied by GTP or GDP. Conversion occurs following receptor activation. Following receptor activation two proteins referred to as Grb2 and SOS (FIG. 14) complex with the receptor. Grb2 serves as a cytoplasmic sensor/translocator and senses ligand induced autophosphorylation. Sos serves as a guanine nucleotide releasing factor and reduces affinity of Ras for GDP but not GTP thus leading to Ras activation. Grb2 and Sos are bound with high affinity SH2 bonds to specific autophosphorylation sites on the receptor. Other molecules are involved in this complex eg phospholipase Cγ (PLCγ) and GTPase activating protein (GAP). GAP a 120 kD protein is activated by phosphorylation and also complexes with the receptor and catalyses the conversion of Ras GTP to Ras GDP (FIG. 15). Gap is therefore considered to occupy a key position in the signal pathways that control growth.

Immunopurification of GAP and Other Protein Substrates

Solubilised MVM (100 µg/30 µl) from newborn pigs were phosphorylated as described above with defatted acellular colostrum (Note: colostrum samples were preabsorbed with 5 mg of protein G and 7.5 mg Protein A each for 2 hours at 4° C. to remove IgG and prevent interference with the immunopurification procedures). After the addition of $^{32}$P-ATP GAP was isolated with mouse anti-GAP MAb (purchased from Upstate Biotechnology Incorporated, Lake Placid, N.Y.). GAP Mab was added (10 µg/10 µl) to each of 4 membrane samples (4×100 µg protein) and incubated for 4 hours at 4° C. Following incubation 2 mg of protein G was added and the samples incubated for a further 4 hours at 4° C. The samples where then transferred to mobitec filter columns (Mobitec, Gottingen, Germany) and the columns washed extensively with 50 column volumes of Buffer B. The bound proteins were recovered using 3×Laemmli buffer and resolved on 10% SDS-polyacrylamide gels. FIG. 16 demonstrates that Ras/GAP is activated following colostrum stimulation. The appearance of multiple phosphorylated proteins is consistent with immunopurification of a receptor complex. FIG. 17 illustrates the identification of two cytoskeletal hyerphosphorylated substrates namely annexin and cytokeratin.

EXAMPLE 3

Isolation and Characterisation of a Colostral-derived Growth Factor

Comparison with Known Growth Factors

The CDGF induced a very reproducible and potent stimulation of phosphorylation of microvillar membrane proteins. The pattern of phosphorylation was compared with known growth factors in an attempt to identify the activity. IGF-1 has already been shown to phosphorylate newborn and suckled MVM proteins but the patterns were quite distinct. Equally in vivo experiments investigating the effect of oral administration of IGF-1 to colostrum-deprived (CD) and colostrum-fed (CF) piglets served to illustrate that although IGF-1 can modulate intestinal function, the biological action of colostrum cannot be mimicked by IGF-1. In summary, IGF-1 prevented the normal cellular decline of lactase and retarded the expression of α2,3-sialylation in the CD but not CF pigs (FIGS. 18, 19). (Kelly et al. 1994) Numerous other growth factors have been screened using the phosphorylation assay. To date, no growth factor has been screened which exhibits the same or similar action as CDGF. FIG. 20 illustrates a comparison with EGF, Insulin, TGF and their synergistic actions with CDGF. Growth hormone, bombesin, lactoferrin etc. have also been screened.

Concentration of CDGF During Lactation

CDGF is present at highest concentration in colostrum and declines significantly as lactation progresses. The activity of colostrum can be diminished to neglible levels at a 100 fold dilution. (FIG. 21). Milk generated at 7 d lactation contains about 20 fold less CDGF, however, the levels are still physiologically significant. In addition the decline in the concentration of CDGF is consistent with the decreasing trend exhibited by many of the known growth factors.

Chemical Characteristics of CDGF

CDGF is degraded by trypsin confirming its peptide nature. The activity is stable in acid ie. formic and trifluoroacetic acid. Heating for 10 mins at 100° C. appears to result in a minor loss of activity (FIG. 22). The activity of CDGF is preserved in dithiothreitol (DTT), hence disulphide bridges are not relevant to biological activity. Combination of these treatments had little effect on the biological activity but resulted in a significant purification of CDGF. (See FIG. 22B).

Purification of CDGF

First Phase: Size Exclusion Chromatography

Colostrum samples were obtained from sows not later than 8 hours from the onset of farrowing. Colostrum was centrifuged at 27,000 g for 30 minutes and applied to an AcA 34 (acrylamide/agarose) column (exclusion limit 300 kD). Samples were run in 20 mM HEPES buffer pH 7.2 (tissue culture grade). Fractions were pooled, dialysed against distilled $H_2O$ and finally lyophilised. Fractions were reconstituted to the original colostrum concentration and the biological activity determined using the phosphorylation bioassay. Activity was located in the high molecular weight fractions of colostrum (FIG. 23). FIG. 24 illustrates the phosphorylation activity associated entirely with F5.

As described at the outset peptide growth factors are considered to be in the molecular range 3–80 kD. The factor isolated eluted in the void volume suggesting that it size was at least 250 kD. To date, no growth has been isolated of this size although a novel TGFβ has been recently described of 150 kD. It was therefore hypothesized that CDGF like many other peptide growth factors is a smaller peptide but is present in colostrum in association with a larger binding protein.

Second Phase: Reverse Phase Chromatography

To assess the validity of the above hypothesis namely that CDGF is bound to a binding protein and is itself of lower molecular size, two further purification procedures were undertaken. The first involved reverse phase chromatography. Fraction F5 isolated from the gel filtration column and identified with biological activity (as determined using the phosphorylation assay) was resuspended in 0.1% Trifluoroacetic Acid (TFA) in order to dissociate it from its binding protein. The fraction was then applied to a Bond Elut C18 column previously prepared by presoaking with Acetonitrile (ACN) (Far UV grade) and 0.1% TFA. (Note these columns bind larger molecular proteins irreversibly). The column was then eluted with a gradient of 90% 0.1% TFA/10%ACN to 20% TFA/80% ACN. The eluted fractions were evaporated to dryness in the presence of 0.2% Bovine Serum Albumin (BSA) and then reconstituted in distilled $H_2O$. Active peptide was found to elute between 30–50% ACN (FIG. 25).

Third Phase: HPLC Purification in the Presence of the Chaotropic Agent Guanidine Hydrochloride To provide an indication of the molecular size of the peptide, fraction F5 from the gel filtration column was resuspended in 0.1% TFA and injected on to a HPLC BioSep SEC 2000 column (Phenomenex). The sample was run in the presence of 5M Guanidine Hydrochloride and all peaks were collected. The eluate from ten independent injections were pooled. Each fraction was then washed extensively using 1K Filtron concentrators in order to desalt (residual guanidine was <5 pM) and the sample concentrated from an initial volume of approximately 40 ml to 200 µl. The fractions were then evaporated to dryness in the presence of 0.2%BSA and reconstituted in distilled water. The activity was located in fraction 2 (elution time 13.5–14.5 minutes) (FIG. 26). FIG. 27 illustrates the phosphorylation activity associated entirely with F2. Previous calibration of the column under the exact running conditions adopted for the purification of the peptide revealed that the molecular size is approximately 70 kD. The precise molecular mass of the peptide requires the sequence data or Matrix-assisted laser desorption ionisation, time of flight (MALDI-TOF) spectrometry.

EXAMPLE 4

Biological Activity

Demonstration of Growth Factor Action

The ultimate classification of a peptide as a growth factor is the demonstration of its growth promoting action on cells in culture. The CDGF was derived from porcine colostrum, currently a porcine intestinal cell line does not exist. However, a cell line isolated from rat intestinal crypt cells namely IEC 6 was used to investigate the mitogenic activity of CDGF. Cells were seeded at 10,000 cells per well of a 24 well Corning plate in 1 ml Dulbeccos Modified Eagles medium DMEM containing 5% foetal calf serum (FCS), 2 mM L-glutamine and penicillin/streptomycin antibiotics. After 16 hour growth the cells were stepped down into DMEM containing 10 µg/ml transferrin and 0.2 µg/ml sodium selenite for at least 24 hour. The cells were then stimulated with 5% FCS, 10% defatted acellular colostrum and 10% CDGF for 20 hours after which 2 µci $^3$H-thymidine was added to each well for a further 4 hour. Cells were then washed in Hanks balanced salt solution, fixed in methanol, TCA precipitated and NaOH solubilised. Incorporated radioactive thymidine was then counted using a β-counter. CDGF was found to stimulate IEC 6 cells significantly above the controls and in fact in some experiments above that of colostrum (FIG. 28).

Comparison with Known Growth Factors

The activity of CDGF was compared with known growth factors which also mediate their effects through tyrosine kinase receptors ie. EGF, IGF, FGF and PDGF. These factors were either supplied to the cells in isolation or in combination at concentrations ranging from nanomolar to micromolar. The known growth factors tested were unable to mimic CDGF (FIG. 29, 30). Experiments have also shown that CDGF can promote the growth of the human intestinal Caco-2 cell line, a human colon carcinoma cell line. CDGF can therefore produce biological effects on intestinal cell lines derived from different species ie. rat, pig and human.

Biological Activity of CDGF Downstream of Ras

One approach to understand the genetic base for the proliferation and differentiation of cells in response to growth factors is to monitor gene activation. The Ras pathway has been linked to the induction of the early response genes c-myc and fos (FIG. 31). The ability of CDGF to stimulate gene expression was investigated using both the rat IEC 6 and the human Caco-2 cell lines. The culture conditions were identical to that described above except that the cells were seeded onto 90 cm Greiner culture plates. The cells were stimulated with colostrum and CDGF in the presence of 10 µg/ml of cyclohexamide for 2 hours and compared to a control grown in the presence of DMEM supplemented with transferrin and selenium. To investigate the superinduction of early response genes c-myc and fos, RNA was extracted using the methodology of Chomczynski and Sacchi and early response gene expression monitored using Northern hybridisation. Preliminary data confirmed that CDGF stimulates mRNA for fos and c-myc (Result not shown).

What is claimed is:

1. A purified colostrum derived growth factor (CDGF) of porcine origin, said factor having a molecular size of 60–80 kDa and being hydrophobic, wherein the ability of the factor to promote phosphorylation of membrane proteins of microvillar membrane vesicles:
   i) is abolished by trypsin;
   ii) is retained after heating to 100° C. for 10 minutes;
   iii) is retained in 2.4M formic acid;
   iv) is retained in 100% of 0.1% trifluoroacetic acid;
   v) is retained after treatment with dithiothreitol;
   vi) is retained in 50% acetonitrile; and
   vii) is retained in 50% ethanol,
   wherein said factor is soluble in 100% of trifluoroacetic acid and is soluble in 50% ethanol.

2. A factor as claimed in claim 1 wherein the factor possesses at least one activity selected from the group of activities consisting of:
   i) stimulate proliferation of intestinal cells in in vitro cultures;
   ii) promote differentiation of intestinal cells as measured by lactase activity and protein glycosylation;
   iii) phosphorylate membrane proteins of MVM vesicles in a phosphorylation assay;
   iv) stimulate the Ras pathways via GAP in MVM vesicles; and
   v) stimulate genes of c-myc and fos.

3. Process for the preparation of a factor as claimed in claim 1, comprising the steps of:
   a) separating all the components of colostrum having a molecular weight of over 200 kDa and discarding components having a lower molecular weight;
   b) treating the product of step a) with dithiothreitol and boiling for approximately 10 minutes; and
   c) centrifuging the mixture of step b) to spin down precipitated matter and separating off the supernatant containing the factor.

4. A therapeutic composition comprising a factor according to claim 1 together with at least one inert carrier or excipient.

5. A therapeutic composition as claimed in claim 4 further comprising a second active ingredient selected from the group consisting of IGF, EGF, FGF, PDGF, cytokines and antibiotics.

6. A therapeutic composition as claimed in claim 4 formulated as a food supplement or food substance.

* * * * *

UNITED STATES PATENT AND TRADEMARK OFFICE
CERTIFICATE OF CORRECTION

PATENT NO.   : 6,277,813 B1                                     Page 1 of 1
DATED        : August 21, 2001
INVENTOR(S)  : Kelly It is certified that error appears in the above-identified patent and that said Letters Patent is hereby corrected as shown below:

Title page,
Item [86], line 1 should read -- [86]   PCT No.:   PCT/GB96/01686 --

Signed and Sealed this

Sixteenth Day of April, 2002

Attest:

JAMES E. ROGAN
*Attesting Officer*   *Director of the United States Patent and Trademark Office*